US011742067B2

(12) United States Patent
Flaherty

(10) Patent No.: US 11,742,067 B2
(45) Date of Patent: *Aug. 29, 2023

(54) PREDICTABLE AND ADAPTIVE PERSONAL FITNESS PLANNING

(71) Applicant: NIKE, Inc., Beaverton, OR (US)

(72) Inventor: Ryan Flaherty, Encinitas, CA (US)

(73) Assignee: NIKE, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/379,455

(22) Filed: Jul. 19, 2021

(65) Prior Publication Data

US 2022/0013210 A1   Jan. 13, 2022

Related U.S. Application Data

(63) Continuation of application No. 16/518,012, filed on Jul. 22, 2019, now Pat. No. 11,074,999, which is a continuation of application No. 15/016,043, filed on Feb. 4, 2016, now Pat. No. 10,409,961.

(60) Provisional application No. 62/111,959, filed on Feb. 4, 2015.

(51) Int. Cl.
*G16H 20/30* (2018.01)
*G16H 20/40* (2018.01)

(52) U.S. Cl.
CPC ............. *G16H 20/30* (2018.01); *G16H 20/40* (2018.01)

(58) Field of Classification Search
USPC ............................................ 434/247; 463/42
See application file for complete search history.

(56) References Cited

U.S. PATENT DOCUMENTS

| 8,152,693 | B2 | 4/2012 | Nurmela et al. |
|---|---|---|---|
| 8,257,228 | B2 | 9/2012 | Quatrochi et al. |
| 10,409,961 | B2 | 9/2019 | Flaherty |
| 11,074,999 | B2 | 7/2021 | Flaherty |
| 2009/0233771 | A1 | 9/2009 | Quatrochi et al. |
| 2012/0196256 | A1 | 8/2012 | Maeueler et al. |

(Continued)

OTHER PUBLICATIONS

"U.S. Appl. No. 15/016,043, 312 Amendment filed Jul. 11, 2019", 6 pgs.

(Continued)

*Primary Examiner* — Pierre E Elisca
(74) *Attorney, Agent, or Firm* — Schwegman, Lundberg & Woessner, P.A.

(57) ABSTRACT

Systems, methods, devices, and computer programs for generating personalized fitness programs are disclosed. One aspect comprises a method including inducing a release of a protein expression into the body, measuring a force generated by the body utilizing over ninety percent of skeletal muscle to generate the force, determining a force metric based on the force generated in relation to a parameter of the body, identifying a target force metric based on at least one user identified target metric, measuring at least one physical metric of the body, generating personalized training regimen based on the determined force metric and the at least one identified target metric, the developed training regimen configured to maximize conversion of type 1 muscle cells to type 2b muscle cells, and wherein the personalized training regimen is designed to be implemented by the body while the protein expression is present in the bloodstream of the body.

20 Claims, 17 Drawing Sheets

(56) References Cited

U.S. PATENT DOCUMENTS

| | | | |
|---|---|---|---|
| 2013/0095459 A1 | 4/2013 | Tran | |
| 2013/0171599 A1 | 7/2013 | Bleich et al. | |
| 2014/0336947 A1 | 11/2014 | Walke et al. | |
| 2015/0125832 A1 | 5/2015 | Tran | |
| 2016/0160211 A1 | 6/2016 | Huge et al. | |
| 2016/0189534 A1* | 6/2016 | Wang | G08C 17/00 340/870.39 |
| 2016/0220867 A1 | 8/2016 | Flaherty | |
| 2018/0220967 A1* | 8/2018 | Wang | A61B 5/1477 |
| 2019/0146480 A1* | 5/2019 | Cella | G05B 19/41865 702/188 |
| 2019/0187681 A1* | 6/2019 | Cella | G06N 20/00 |
| 2019/0303807 A1* | 10/2019 | Gueye | G06Q 20/3224 |
| 2020/0051682 A1 | 2/2020 | Flaherty | |

OTHER PUBLICATIONS

"U.S. Appl. No. 15/016,043, Examiner Interview Summary dated Oct. 11, 2018", 3 pgs.

"U.S. Appl. No. 15/016,043, Final Office Action dated Jul. 18, 2018", 8 pgs.

"U.S. Appl. No. 15/016,043, Final Office Action dated Oct. 24, 2018", 8 pgs.

"U.S. Appl. No. 15/016,043, Non Final Office Action dated Dec. 13, 2017", 11 pgs.

"U.S. Appl. No. 15/016,043, Notice of Allowance dated Apr. 11, 2019", 5 pgs.

"U.S. Appl. No. 15/016,043, PTO Response to Rule 312 Communication dated Aug. 5, 2019", 2 pgs.

"U.S. Appl. No. 15/016,043, Response filed Mar. 25, 2019 to Final Office Action dated Oct. 24, 2018", 11 pgs.

"U.S. Appl. No. 15/016,043, Response filed May 11, 2018 to Non Final Office Action dated Dec. 13, 2017", 17 pgs.

"U.S. Appl. No. 16/518,012, Non Final Office Action dated Aug. 25, 2020", 7 pgs.

"U.S. Appl. No. 16/518,012, Notice of Allowance dated Mar. 12, 2021", 9 pgs.

"U.S. Appl. No. 16/518,012, Preliminary Amendment filed Nov. 5, 2019", 7 pgs.

"U.S. Appl. No. 16/518,012, Response filed Jan. 25, 2021 to Non Final Office Action dated Aug. 25, 2020", 9 pgs.

* cited by examiner

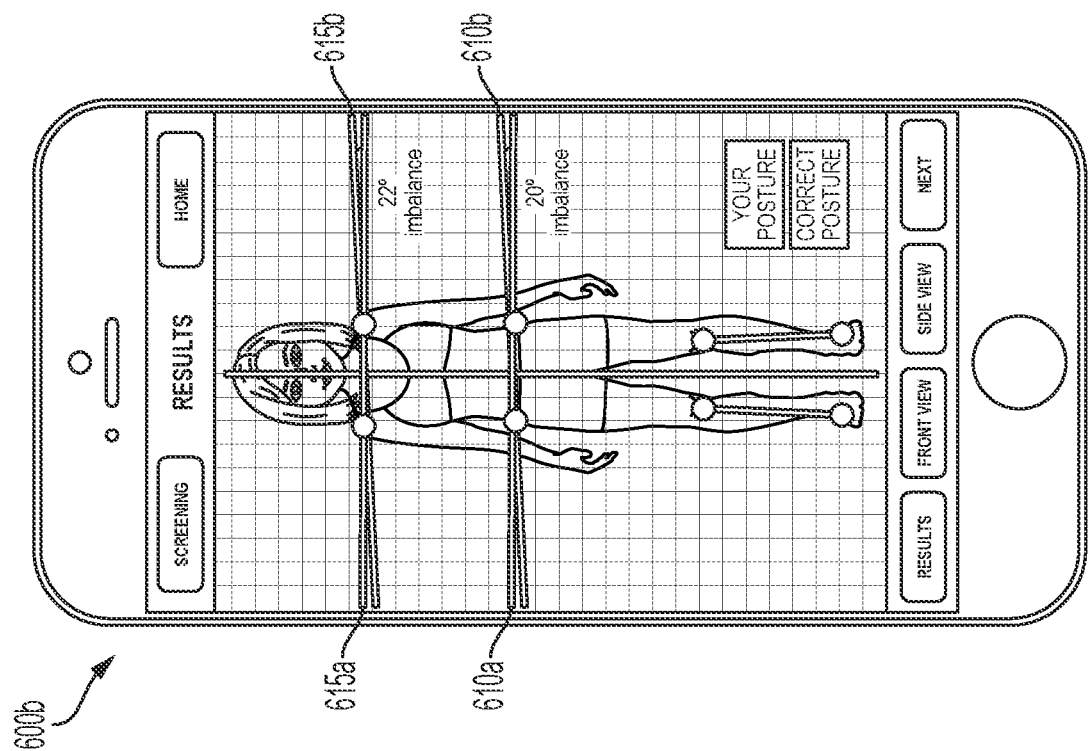
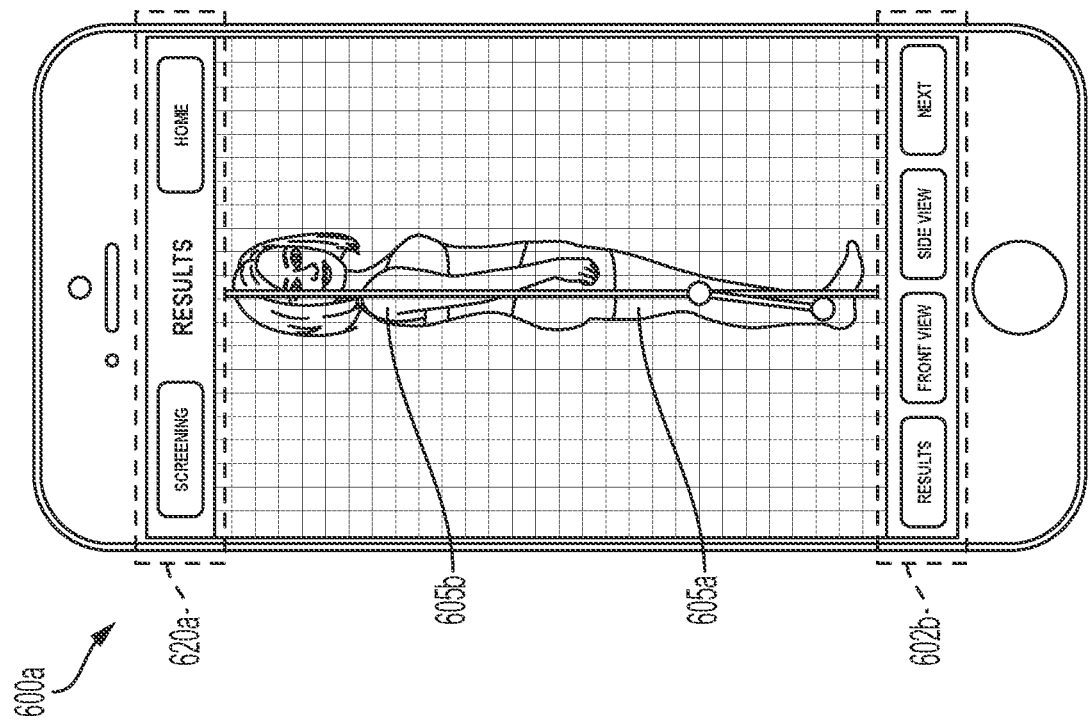
FIG. 6

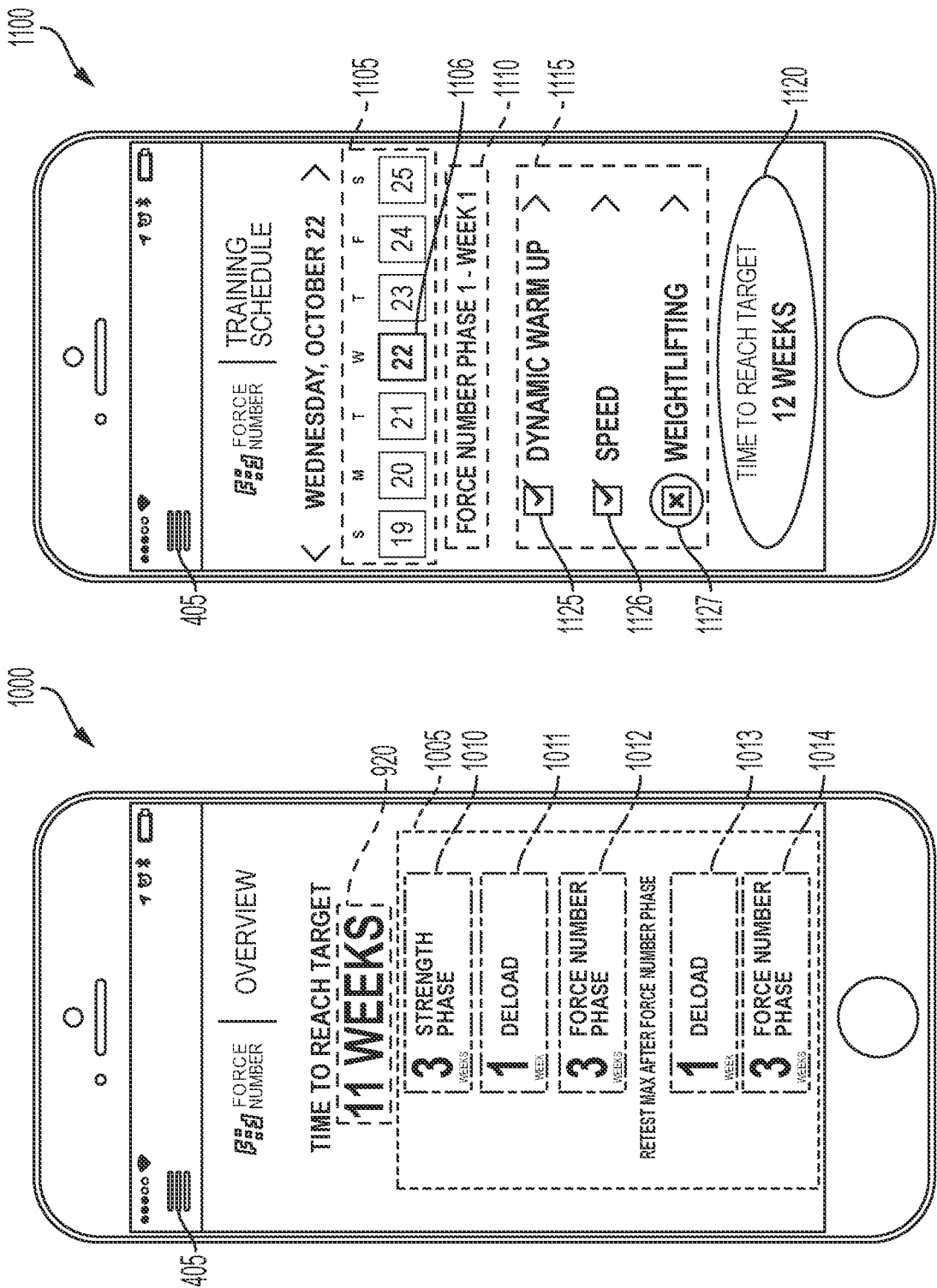

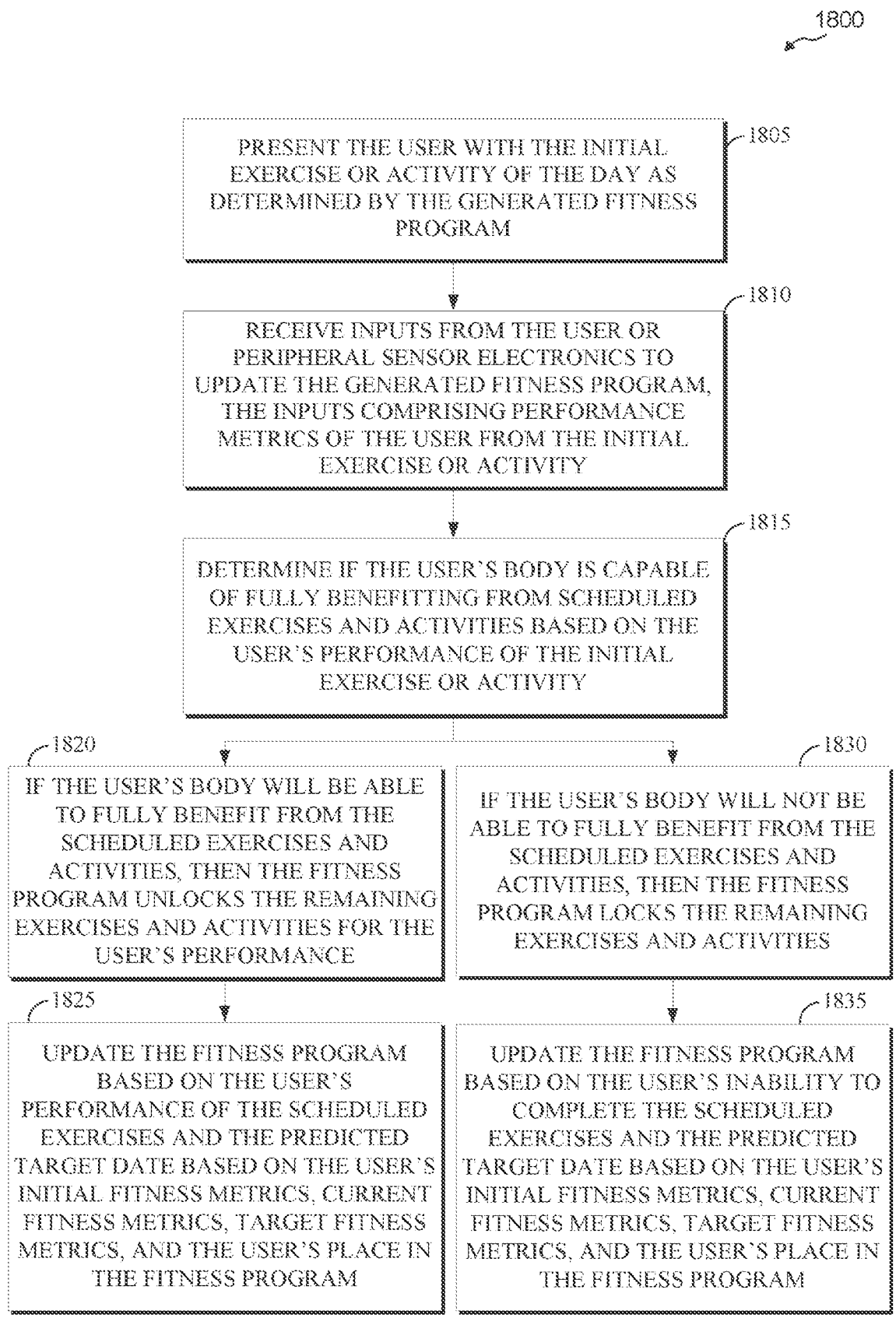

PREDICTABLE AND ADAPTIVE PERSONAL FITNESS PLANNING

CLAIM OF PRIORITY

This application claims priority to U.S. Provisional Application No. 62/111,959 entitled "PREDICTABLE AND ADAPTIVE PERSONAL FITNESS PLANNING" filed Feb. 4, 2015, the disclosure of which is hereby incorporated by reference in its entirety.

BACKGROUND

The present application relates generally to personalized fitness programs and exercise regimens, and more specifically to systems, devices, and methods for the development, implementation, and tracking of personal fitness programs and exercise regimens.

Personalized fitness programs can be highly complex and can involve various facets of an individual's life. Some personalized fitness programs may focus on exercise routines or training systems, while other fitness programs may provide physical training, fitness programs, or workout regimens based a predetermined schedule of activities given the general results for an average sampling of users. Users may utilize fitness programs focusing on physical training, individual abilities, or workout regimens to identify a user's current physical capabilities and to generate fitness programs based on the user's current physical capabilities with a desired physical capabilities improvement. However, improving the user's physical capabilities may prove difficult or uninspiring for users using current health programs that are unable to provide accurate predictions for the user's expected results or efficiently obtain results after using the health program. Accordingly, health programs capable of integrating sensors configured to identify and measure user's physical capabilities with the development of a training regimen capable of accurately predicting the user's physical progression and expected results after use of the health programs are desired.

SUMMARY

The systems, methods, devices, and computer program products discussed herein each have several aspects, no single one of which is solely responsible for its desirable attributes. Without limiting the scope of this invention as expressed by the claims which follow, some features are discussed briefly below. After considering this discussion, and particularly after reading the section entitled "Detailed Description," it will be understood how advantageous features of this invention include, among other things, efficient provisioning of personalized fitness information, predicting the user's physical metrics after using the fitness program, and improving the user's physical metrics.

BRIEF DESCRIPTION OF THE DRAWINGS

The accompanying drawings, together with the specification, illustrate exemplary embodiments, and, together with the description, serve to explain the principles of the present disclosure.

FIG. 6 shows an example of two screenshots of two postural evaluation screens of the software application that may be active on the device of FIG. 2, in accordance with an exemplary embodiment.

FIG. 10 shows an example of a screenshot of a fitness program overview screen of the software application that may be active on the device of FIG. 2, in accordance with an exemplary embodiment.

FIG. 11 shows an example of a screenshot of a training schedule overview screen of the software application that may be active on the device of FIG. 2, in accordance with an exemplary embodiment.

FIG. 18 shows a flow chart providing details of a method for updating or modifying the fitness program described in the methods of FIG. 16 and FIG. 17, in accordance with an exemplary embodiment.

DETAILED DESCRIPTION

Figure 1:
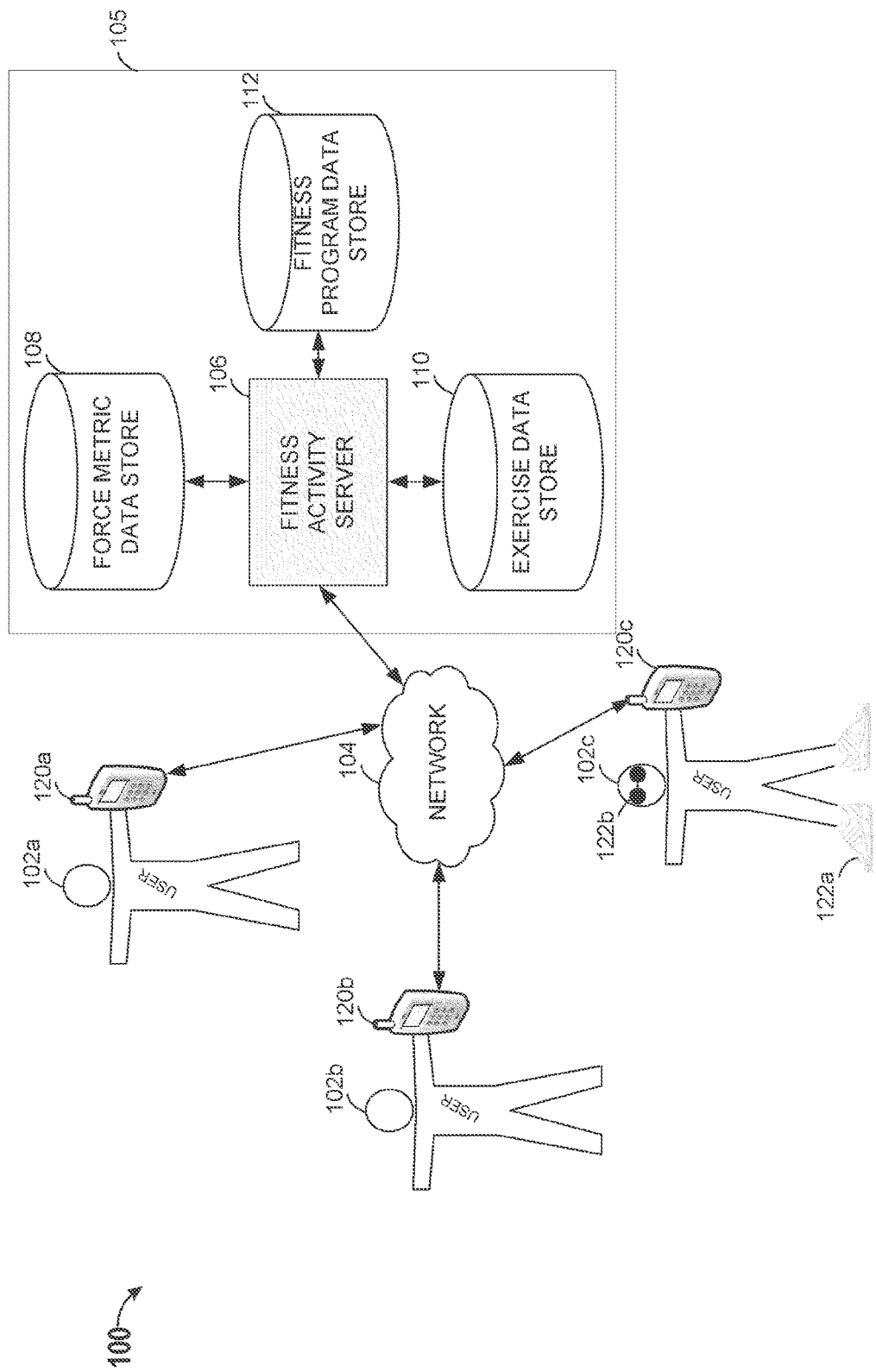
FIG. 1 is a network diagram illustrating one embodiment of a personalized fitness system, in accordance with an exemplary embodiment.

The present disclosure generally relates to systems, devices, and methods for generating and implementing personalized fitness programs configured to receive and utilize information from external sensors (for example, force sensors in shoes) and predict a user's results after using the personalized fitness programs.

How a body responds to a physical fitness regime can vary from person to person. Physiological, genetic, and other factors can influence the effects of exercises on a person. When the body is subjected to an exercise, a complex sequence of events occurs in the body which ultimately causes a change in the body. As the body releases certain chemicals, the efficacy of a training session may hinge on stimulating the body during the period when concentrations of such chemicals are heightened to ensure optimal training benefits. For example, some exercises may place more stress on the body than others. Some exercises may be designed to utilize over 90% of the body's skeletal muscle, which may stimulate the body's production of a protein that may greatly increase the efficacy of the training session. For example, when over 90% of the body's skeletal muscle is used, the body may produce the CRTC2 protein, which may strengthen and increase energy efficiency. Additionally, the body may recruit available Type 2b muscle cells, which may have four times the force output of Type 1 muscle cells. Additionally, such exertion of the body's skeletal muscle may also trigger additional lactate transporters to better accommodate toxins released intermuscularly while and after being exerted. When the user participates in an exercise program while the CRTC2 protein is present in the body, the user may maximize the conversion of Type 1 muscle cells to Type 2b muscle cells.

Additionally, the physical fitness regime may comprise multiple exercises that may have different goals. For example, one or more exercises of the physical fitness regime may be intended to improve a user's strength (for example, a hex bar deadlift exercise), while other exercises may be intended to improve aerobic processes or prevent injury in the user (for example, running or stretching exercises). Thus, in a single day or over the course of the fitness program, the user may perform a variety of exercises intended to target or improve the user's fitness metrics and improve the user's ability to perform without being injured due to imbalances and weaknesses of their body.

The features described provide a determination of how and when to stimulate the body to obtain maximum results for an exercise or regimen of exercises for a specific individual. One-size-fits-all exercise programs may not take into account the activity, body characteristics, and past, present, and/or future activities of a user when providing an exercise schedule. Accordingly, the features discussed in further detail below provide an accurate metric for an individual's fitness level, generate an exercise program which is tailored not only to the fitness level but also a specified fitness goal and activity, and provide dynamic adjustments to the exercise program by tracking on-going activities for the user. Additionally, the one-size-fits-all exercise programs may not be able to accurately predict results that consider data received from external sensors (for example the shoe sensors) or other sources and may be unable to provide guaranteed improvements to the user's starting metrics.

The features described also provide a method for generating a fitness program for a user. The method may comprise receiving information accounting for the user's goals, current body characteristics, current sports or activities, and the user's current physical metrics and target metric(s). The method may then generate an initial schedule of exercises and other physical activities that will help the user improve the physical metrics and attain the established goals and target metrics in a predictable fashion. The schedule of exercises and physical activities may be selected based on the user's goals and current physical metrics and body characteristics. In some embodiments, the method may detect physical activity performed by the user and update the initial schedule according to the activity performed. For example, the physical activity may comprise exercises or activities that are part of the initial schedule. In some embodiments, the physical activity may comprise exercises or activities in addition to or instead of those generated as part of the initial schedule. Accordingly, the method may automatically adjust the initial schedule to generate a revised schedule, based on the detected physical activity. In some embodiments, the adjustment of the initial schedule may involve reorganizing the existing exercises and activities into a new order or schedule. Some adjustments of the initial schedule may involve changing, eliminating, or adding a scheduled activity, for example adding an additional running exercise or weight lifting exercise or adjusting the parameters for a scheduled activity, for example adjusting the speed on a scheduled run or the number of repetitions for a weight lifting exercise. In some embodiments, the method may receive inputs from the external sensors (e.g., shoe force sensors or similar sensors) and "unlock" a given exercise or scheduled activity according to the user's performance. For example, to access a day's scheduled activities, the user may be required to perform a first activity or exercise, for example, a hex bar deadlift routine. Based on the user's performance, as detected by the external sensors (for example, the shoe sensors), the fitness program may restrict or allow the user's ability to access and perform the remaining scheduled activities for the day. In some embodiments, the user may be restricted from accessing and performing the scheduled activities because the detected performance may indicate that the user's body is not sufficiently rested or will not benefit fully from the scheduled activities for some reason. If the user's detected performance indicates that the user will fully benefit from the scheduled activities, then the user may be allowed to access and perform the scheduled activities.

The features described may also provide integration of the generated exercise schedules with a calendar or other software that may be shared by the device on which the exercise program may operate. For example, the generated exercise schedule may be merged or synchronized with the user's general calendar (or non-exercise program calendar) and may be configured to provide the user with prompts or reminders regarding scheduled exercises and/or activities. In some embodiments, the exercise program may be configured to monitor the user's general calendar and generate or adjust the initial calendar based on activities scheduled or noted on the user's general calendar. In some embodiments, the exercise program may integrate with social media applications or other messaging software and may use these other applications and software to remind the user of scheduled exercises or update the schedule once the user completes a scheduled exercise or activity or performs an unscheduled exercise or activity.

More specifically, the features may provide personalized fitness programs and software applications capable of receiving personal information from a user and using the received personal information in conjunction with goals established by the user to generate a personalized fitness routine. The personalized fitness routine may include one or more exercise regimens developed to elicit the user's maximum effort over a calculated timeframe to reach the user's goals. The personalized fitness routine may receive inputs from the user and from various devices (for example, external shoe sensors or internal physical sensors or imaging equipment) to generate the exercise regimen to be most beneficial and efficient for the user. Once the exercise regimen is generated, the inputs from the user and from various devices may be used to monitor the user's progress through the personalized fitness routine. Based on the user's progress through and completion of exercises in the fitness routine, the personalized fitness program may modify the fitness program according to the user's demonstrated physical capabilities. In short, the aspects described may provide users with a flexible method, system, and program configured to identify the user's physical capabilities and provide a structured and predictive fitness program that allows the user to achieve desired, personalized fitness goals in an efficient, healthy, and fulfilling manner.

In one aspect, a system including a centralized server and a remotely accessible client device configured with a software application may generate, monitor, and modify a user's fitness routine. The server may receive the user information via communications with the software application via the client device and may generate the fitness program for the user accordingly. The server may then communicate specifics of the fitness program (for example, an exercise regimen, a predicted timeline, etc.) to the software application via the client device for presentation such as to the user. The generated fitness program may be over 99% reliable in helping the user attain the desired goals by the predicted timeline. The software application via the client device may assist the user's progress through the fitness program, for example providing the user with a schedule, including instructions for completing the scheduled exercises, providing real-time coaching on the user's performance in the scheduled exercises (for example, recommending changes in form or providing motivational messages), monitoring the user's performance by tracking inputs from various sensors (internal or external) and/or input/output components of the mobile device on which the app is operating (for example, a camera, microphone, speaker, display, etc.). Throughout the user's participation in the fitness program, the software application may cause the client device to communicate the user's progress to the server, and the server may modify the fitness program according to the user's progress. Once the user attains the desired goal by the predicted timeline, the server may terminate the fitness program.

One non-limiting advantage of the described features may include the ability to predict, with over 99% certainty, the amount of time needed for a generated fitness program to allow the user to progress from an initial set of physical performance metrics to a desired set of physical performance metrics. An additional benefit may include the ability for the system to generate a personalized fitness program based on the user's initial physical capabilities and the user's target goals, where the fitness program is personalized based on the user's initial physical capabilities and physical metrics to provide exercises and recommendations to reach the target goals within the target deadline. Unlike other systems which are unable to accurately predict the user's end results or require users to have expensive equipment, have substantial knowledge of kinesiology or exercise physiology, and/or laboriously enter volumes of data, this system is based on basic, initial inputs that most users know (for example, age, weight) and utilizes equipment that is often readily available. From these basic, initial inputs, the expert system may tailor a personalized fitness program for a user which is over 99 percent effect in assisting the user to attain his/her goals.

This allows the user to more effectively and efficiently utilize their exercise time and minimize adverse effects of existing exercise programs.

FIG. 1 shows an embodiment of a network diagram 100 of a personalized fitness program generation and implementation system, in accordance with an exemplary embodiment. As shown in FIG. 1, multiple users 102a-102c may each have a mobile device 120a-120c configured to connect to a network 104. In some embodiments, the user 102c may comprise one or more peripheral devices. As shown in FIG. 1, the peripheral devices may comprise a pair of shoes 122a or glasses 122b (collectively or individually referred to hereafter as "the peripheral device 122" or "the peripheral devices 122") that comprises one or more sensors configured to measure forces or other user metrics. In some embodiments, the one or more sensors of the peripheral device 122 may be configured to interface and communicate with the mobile device 120c of the user 102c The network 104 may connect the mobile devices 120a-120c to a fitness program system 105. The fitness program system 105 may comprise a fitness activity server 106, a force/metric data store 108, an exercise data store 110, and a fitness program data store 112. The arrows shown between the mobile devices 120a-120c and the network 104, the network 104 and the fitness program system 105, the fitness activity server 106 and the force/metric data store 108, the fitness activity server 106 and the exercise data store 110, and the fitness activity server 106 and the fitness program data store 112 may represent communications between the various devices and components of the network diagram 100. The communications indicated may be either bidirectional or unidirectional and any communication method may perform the communications indicate, for example IEEE 802.15 compliant Bluetooth) communications, IEEE 802.11 standard compliant Wi-Fi communications, IEEE 802.3 Ethernet communications, near-field communications, or equivalents thereof. In some embodiments, a bus system may perform the communications. For example, the communications between the fitness activity server 106, the force/metric data store 108, the exercise data store 110, and the fitness program data store 112 may occur via a single bus system when these components are all part of a single or integrated system such as the fitness program system 105.

The mobile devices 120a-120c may be configured to display or otherwise communicate information between the respective users 102a-102c and the fitness program system 105 via the network 104. For example, the mobile devices 120a-120c may function as an interface between the users 102a-102c and the fitness program system 105. In some embodiments, the users 102a-102c may use the mobile devices 120a-120c to input information to the fitness program system 105 and/or view information from the fitness program system 105. For example, the mobile devices 120a-120c may provide to the fitness program system 105 an initial force metric or other physical metrics or personal account information for the respective user 102a-102c. The fitness program system 105 may generate a fitness program for the user based on these initial metrics. Additionally, or alternatively, the mobile devices 120a-120c may be configured to monitor a user's progress through the generated fitness program. In some embodiments, the mobile devices 120a-120c may be configured to perform real-time tracking of progress through scheduled exercises or to show progress or scheduling updates to the users 102a-102c pertaining to the generated fitness program. The tracking by the mobile devices 110a-120c may include tracking non-scheduled activities, such as number of steps, impromptu running, or the like. The tracking may utilize one or more sensors integrated in the mobile device such as an accelerometer, a camera, or a microphone. The tracking, in some implementations, may be based on sensor data received by the mobile device from an external sensor in data communication with the mobile device.

In some embodiments, the mobile devices 120a-120c may comprise one of a cellular phone, a multimedia device, a watch, a PDA, or any other portable electronic device capable of communicating with other electronic devices in a wired or wireless manner. In some embodiments, the mobile devices 120a-120c may comprise devices capable of operating a software application (app) or program, wherein the app may be configured to generate, implement, and/or monitor a fitness program stored locally or on a remote device, for example, the fitness program system 105, for one or more users 102a-102c. In some embodiments, the app may interact with the mobile devices 120a-120c, the one or more peripheral devices 122, and the network 104 and allow for user interaction directly via one of the mobile devices 120a-120c or the peripheral device 122. The connection of the mobile devices 120a-120c to the network 104 may allow the users 102a-102c to remotely interact with the fitness program via an external or third-party device or program. In some embodiments, the mobile devices 120a-120c may be configured to store data for later transmission via the network 104, for example, when the mobile devices 120a-120c are not capable of wireless or wired communications with the network 104 without additional hardware (for example, a PDA that may need to be placed in a dock before it is capable of network communications on the network 104).

In some embodiments, the user 102c may utilize the peripheral electronic device 122, which may be configured to interface or couple with the mobile device 120c, the network 104, or an external electronic device (not shown in this figure). As shown in FIG. 1, the peripheral electronic device 122 may be shown as a pair of glasses or a shoe containing sensors on the user 102c. As described above, the peripheral electronic device 122 may be configured to interface or couple with the mobile device 120c via Bluetooth, Wi-Fi, or any other wireless or wired means of data communication. The peripheral electronic device 122 may include one or more sensors configured to count footsteps, measure force exerted, measure distance traversed in a step, measure height or distance jumped, or measure or count any other physical or force metric obtained via any body or other physical or electrical sensors (for example a heart rate, oxygen levels in blood, etc.). Once the counting or measuring is complete (or while the counting or measuring is continuously being updated), the peripheral electronic device 122 may be configured to communicate the counted or measured information to the mobile device 120c via the interface described above. For example, in operation, the peripheral electronic device 122 may be configured to interact with the user 102c by counting a number of steps taken by the user 102c and communicating the count to the mobile device 120c or to a destination on the network 104. In some embodiments, the information captured by the peripheral electronic device 122 may be used to update or modify an existing fitness program. Thus, external sensors may couple to the fitness program system. The external sensors may provide to the fitness program system additional metrics and other related information about the user's performance of one or more exercises of the user's personalized fitness program or of the user's performance of one or more exercises or activities in addition to those of the fitness program. In some embodiments, the peripheral electronic device 122 may be configured to integrate with the app operating on the mobile devices 120a-120c. While FIG. 1 depicts the peripheral electronic device 122 as a pair of glasses, in some embodiments, the peripheral electronic device 122 may include sensors embedded within a shoe or pedometer worn on an article of clothing or another part of the body, or a sensor embedded within a wrist-watch or bracelet, or any other electronic device that may be configured to measure or identify physical movement of the user.

The network 104 may be one of the Internet, a local intranet, a local network connection isolated from external access, or any other network structure. As described above, the mobile devices 120a-120c may be configured to communicate on the network 104 via any known means for communicating information. In some embodiments, the network 104 may allow the devices 120a-120c to communicate with each other. In some embodiments, the network 104 may be configured to allow the devices 120a-120c to communicate with the fitness activity server 106. The network 104 may include one or more mediums of communication, wired or wireless, depending on the implementation.

As discussed above, the fitness program system 105 may be configured to receive information from and communicate information to the mobile devices 120a-120c via the network 104. For example, the fitness activity server 106 may receive information such as the user's or the mobile device 120a-120c's identification, which may include information regarding the identity of the user 102a-102c or the mobile device 120a-120c, force metrics or other data related to scheduled exercises, desired target metrics, a request for a new or updated fitness program, or any other information relating to a fitness program associated with the identified user 102a-102e or the identified mobile device 1120a-120c. The fitness program system 105 may use the received information to develop, modify, or track the user's fitness program and progress throughout the user's fitness program.

For example, the fitness program system 105 may receive, via the network 104, the personal identifier associated with the mobile device 120b. The fitness program system 105 may use the received personal identifier associated with the mobile device 120b to access an account for the user 102b in the fitness program data store 112, which may include an existing fitness program. In some embodiments, the fitness program system 105 may further receive acknowledgement of completion of a day's assigned exercises or similar feedback and may update the user's fitness program associated with the user 102b and the mobile device 120b, for example updating a prediction of the expected completion date based on the received information or generating one or more new exercise regimens for the user's fitness program. In some embodiments, the fitness program system 105 may receive a revised target performance metric and may be configured to update the expected completion date or update the user's fitness program based on the new desired target performance metric from the user 102b. The fitness program system 105 may be further configured to transmit a response back to the mobile device 120b indicating the current or new expected completion date of the fitness program and indicating a revised exercise regimen for the fitness program, if applicable.

Accordingly, the fitness program system 105 may be configured to generate, modify, track, or delete a user's fitness program based on the user's current physical abilities or physical condition (as measured by initial or current performance metrics) and a desired physical abilities or physical condition (as measured by desired performance metrics). Based on these initial/current and desired physical abilities or physical condition, the fitness program system 105 may use data from the force/metric data store 108 and exercise data from the exercise data store 110 to generate or modify the user's fitness program, which may be stored in the fitness program store 112. For example, the fitness program system 105 may generate the user's fitness program based, at least in part, on the user's initial and desired (or target) physical metrics. For example, the fitness program system 105 may select the initial exercises of the user's personalized fitness program based on the user's current physical capabilities and may select subsequent scheduled exercises that will help the user reach the desired target metrics.

In some embodiments, the fitness program system 105 may modify generated fitness programs based on inputs or metrics received from the user or from the peripheral electronics 122. For example, based on the inputs or metrics, the fitness program system 105 may determine that the user is performing the generated fitness program according to schedule or may determine that the user is performing ahead of schedule or behind schedule. Accordingly, the fitness program system 105 my automatically update the fitness program schedule or the exercises of the fitness program schedule based on the inputs and metrics received from the sensors of the peripheral electronics 122. For example, when the peripheral electronics 122 detects the user performed a run, the associated metrics may be communicated to the fitness program system 105 so the fitness program system 105 may automatically update the user's fitness program. For example, if the user completes a scheduled run, then the fitness program system 105 may automatically clear the run from the user's fitness program. If the user completes an unscheduled run, then the fitness program system 105 may adjust the user's fitness program to account for the unscheduled activity. This adjustment may comprise deleting one or more scheduled exercises or activities from the user's fitness program. Unscheduled activities or exercises may reduce the amount of time until the user's target metrics are met.

Once the fitness program system 105 completes the generation, modification, tracking, or deletion of the user's fitness program, the fitness program system 105 may generate an output to the network 104 for delivery to the mobile device 120b. For example, the fitness program system 105 may output the generated fitness program to the mobile device 120b via the network 104. Alternatively, the fitness program system 105 may output a confirmation or a congratulatory message in response to receiving an indication that the user completed a scheduled exercise or attained a target metric. In some embodiments, the fitness program system 105 may output the expected completion date of the fitness program for display on the mobile device 120b to the user 102b.

As described briefly above, the force/metric data store 108 and the exercise data store 110 may include various information relating to force metrics and exercises, respectively, and the fitness program data store 112 may include generated profiles and fitness programs associated with users who communicate with the fitness program system 105. In some embodiments, the force/metric data store 108, the exercise data store 110, and the fitness program data store 112 may not be separate data stores but may rather be coupled into a single data store or a combination of shared and separate data stores (not shown in this figure). In some embodiments, the data stored in the force/metric data store 108, the exercise data store 110, and the fitness program data store 112 may be divided into multiple additional data stores (not shown in this figure).

The data stored in the force/metric data store 108 may store data that may correspond to force metrics and associations with fitness capabilities. The force/metric data store 108 (and the exercise data store 110 and the fitness program data store 112) may include a database or similar storage structure that associates a force metric and a user's weight or mass with various performance metrics. For example, the force metric data store 108 may store associations between force metrics and performance metrics. Thus, given the user's performance metric (for example, vertical height jumped), the fitness program system may identify an associated force metric using the user's personal information, and this identified force metric may correspond with the user's force metric. Alternatively, the fitness program may user the user's force metric to identify a specific performance metric (for example, the vertical height the user is capable of jumping or a speed in which the user is capable of running a 40-yard dash, or any other of a number of identified performance metrics). In some embodiments, the fitness program system 105 may be configured to calculate the user's force metric based on information provided by the user and store the calculated force metric in the force/metric data store 108. The fitness program system 105 may use data stored in the force/metric data store 108 to generate or identify a predicted target force metric and one or more predicted performance metrics given a desired performance metric or generated one or more predicted performance metrics from a desired target force metric.

The data stored in the exercise data store 110 may store data related to one or more exercises. For example, the exercise data store 110 may store data regarding the effect of a particular exercise on a user's force metric. This data may include information regarding how the particular exercise effects the user's force metric (for example, the total amount the particular exercise may raise or lower the user's force metric) or how quickly the exercise will have the effect on the user's force metric (for example, if the exercise will raise the user's force metric by 1 point within one week or three weeks). Additionally, the exercise data store 110 may include data of the efficacy of the particular exercise given other performance metrics of the user. For example, the exercise data store 110 may include data indicating that the particular exercise may be more effective for users having stronger upper body strength than users having weak upper bodies (or may be more effective for women than men, etc.). The fitness program system 105 may use the data of the exercise data store 110 in combination with the data from the force/metric data store 108 further in combination with the information provided by the user to generate the fitness program personalized for the user based on the user's desired physical metrics in view of the user's starting physical metrics.

In some embodiments, a new user 102a using mobile device 120a may communicate with the fitness program system 105 via the network 104, requesting the fitness program system 105 generate a fitness program for the user 102a. The fitness program system 105 may generate a fitness program dedicated to the user 102a and store the generated fitness program in the fitness program data store 112. The generated fitness program may comprise one or more different regimens or routines. For example, in some embodiments, the generated (and stored) fitness program may include a user profile for the user 102a and an exercise regimen for the user 102a. In some embodiments, more elements may be included in the fitness program stored in the fitness program data store 112, for example a posture profile and posture correction regimen or a real time training regimen, or any other element that may be associated with a fitness program. The fitness program system 105 may send a profile information request to the user 102*a* requesting information to complete the user 102*a*'s profile. The profile information is described below in more detail with reference to FIG. 4. When the fitness program system 105 receives the profile information from the user 102*a*, the fitness program system 105 may update the user profile of the generated fitness program in the fitness program data store 112.

The fitness program system 105 may also request the user 102*a* provide initial fitness information. The initial fitness information may include one or more of the user 102*s* measured force metric, weight or mass, and performance metrics in a number of fitness activities (for example, a vertical jump height or a 40-yard clash time). The fitness program system 105 may also request the user 102 provide desired fitness goals or targets, for example, a desired target force metric or a desired target performance metric in one or more fitness activities. The fitness program system 105 may use the initial fitness information provided by the user 102*a* with the desired fitness targets provided by the user 102*a* to generate the exercise regimen for the user 102*a*'s fitness program. In some embodiments, the user 102*a* may provide the initial fitness information automatically, and the fitness program system 105 may not send a request to the user 102*a* via the network 104 for the initial fitness information. In some embodiments, the fitness program system 105 may monitor inputs of the user and/or automatically obtain the information. For example, this may be performed by sensors or used by the user that may detect different states of the user and may be able to determine when the user has begun an exercise by detecting certain movements or certain sequence of actions within a fixed time. In some embodiments, the sensors or devices may detect the presence of the user in the vicinity of the sensors or device and automatically begin collecting data and communicating that data to the fitness program system 105.

In generating the fitness program, the fitness program system 105 may communicate with the force/metric data store 108 to identify any values not provided by the user 102*a* that may be useful or necessary in developing the fitness program (for example, force/metric data store 108 may identify the user 102*a*'s mass or weight when provided with the user 102*a*'s force metric and the one or more measured performance metrics or identify the force metric when provided with the user 104's mass or weight and the one or more measured performance metrics, etc.). This information may be useful in generating the user 102*a*'s exercise regimen, where specific exercises in the exercise data store 110 may be determined to be more or less effective based on the initial fitness information of the user 102*a*. Thus, as discussed above, the fitness program system 105 may use information in both the force/metric data store 108 and the exercise data store 110 to develop the exercise regimen associated with the user 102*a*'s fitness program. Additionally, the fitness program system 105 may use the information of the force/metric and exercise data stores 108 and 110, respectively, to predict a timeline or duration of the fitness program. The timeline or duration of the fitness program may represent the time over which the user 102*a* may follow the generated fitness program to progress from the measured performance metric or force metric to the desired target force metric or performance metric.

An exemplary benefit of the fitness program system described herein may be the consistency and uniformity of the provided by the force metrics and fitness program. As will be described in further detail below, the force metric generated and used by the fitness program system 105 for each individual user 102*a*-102*c* may be constant for all users, meaning that the force metric system may be a constant baseline. For example, the user 102*a* having a force metric of 75 as determined by the fitness program system 105 would be capable of generating the same fitness metrics (for example, the same vertical jump height, the same 40-yard dash speed, the same maximum hex bar deadlift weight, etc.) as the user 102*c* having the force metric of 75, regardless of any difference in gender, age, height, weight, etc., between the two users 102*a* and 102*c*. Furthermore, improving the force metric of the user 102*a* by a given amount will take the same amount of time and effort as it would take the user 102*c* to improve from the same initial force metric by the same target amount. Additionally, the base line established by the force metrics between all the users enables the fitness program system 105 to be able to predict the amount of time required to improve between various force metrics. In some embodiments, the improvements between each of the force metrics may take the same amount of time, for example, an improvement from a force metric of 75-80 may take the same amount of time as an improvement from a force metric of 85-90. Accordingly, as the two users 102*a* and 102*c* are on the same baseline created by the force metric system, the fitness program system is capable of generating a predicted target completion time when provided with the user's starting, initial, or current force metric and the user's target force metric.

In some embodiments, the mobile devices 120*a*-120*c* may not need to communicate with the fitness program system 105 to generate, modify, or monitor the user 102*a*-102*c*'s respective fitness program. For example, the components or functionality of the fitness activity server 106, the force/metric data store 08, the exercise data store 110, and the fitness program data store 112 may be integrated into each of the mobile devices 120*a*-120*c*. For example, each of the mobile devices 120*a*-120*c* may include one or more data stores including the information of the force/metric, exercise data, and fitness program data stores 108, 110, and 112, respectively. Accordingly, in some embodiments, the mobile device 120*a* may be configured to generate, store, monitor, and modify one or more of the user 102*a*'s fitness program, profile, or exercise regimen locally without communicating with any external devices, such that all processes related with the personalized fitness program are maintained within the mobile device 120*a*. In some embodiments, the mobile device 120*a* may only use the network 104 to share information or results with other mobile devices 120*b* and 120*c* or other social media forums or to receive updated information to be stored in the force/metric, exercise, or fitness program data stores 108, 110, and 112, respectively.

In some embodiments, the mobile devices 120*a*-120*c* and the fitness program system 105 and any other device not shown in the FIG. 1 may share the functions of generating, monitoring, storing, and modifying the fitness programs of the users 102*a*-102*c*.

Figure 2:
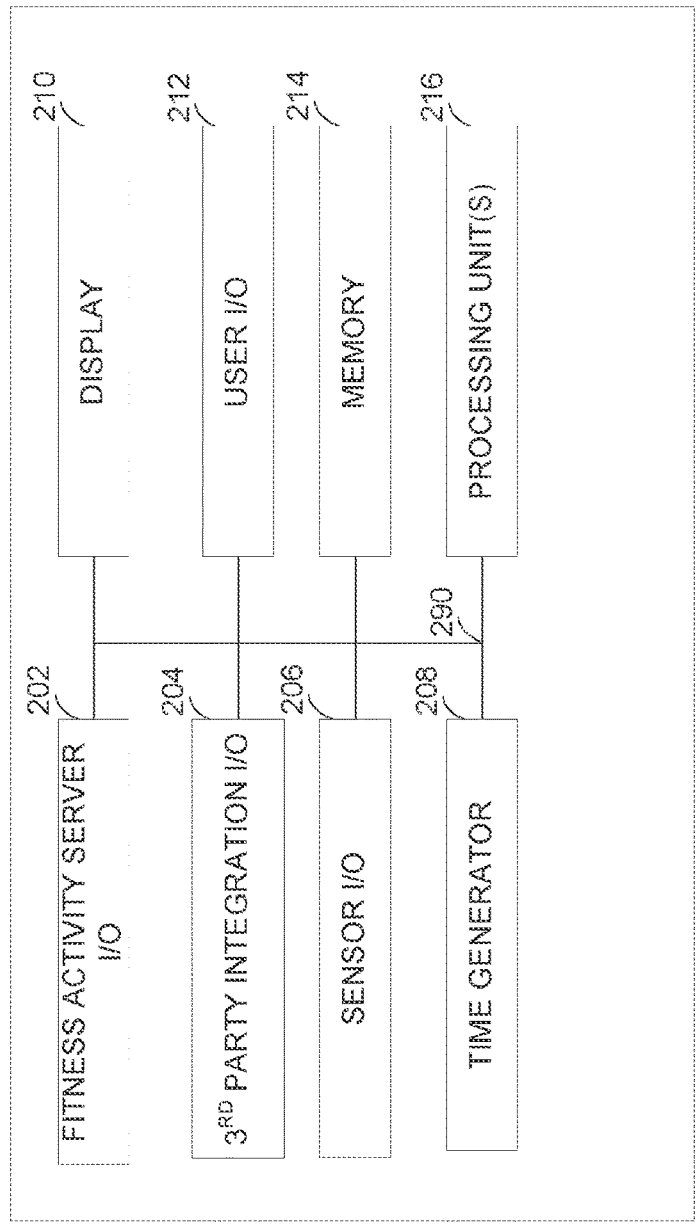
FIG. 2 shows a functional block diagram of an electronic device that may be utilized in the personalized fitness program, in accordance with an exemplary embodiment.

FIG. 2 shows a functional block diagram of an electronic device that may be utilized in the personalized fitness program as described in relation to FIG. 1, in accordance with an exemplary embodiment. In some embodiments, the mobile devices 120*a*-120*c* referenced in FIG. 1 may include the electronic device 200 of FIG. 2. In some embodiments, the fitness program system 105 may include electronic device 200 of FIG. 2. In some embodiments where the electronic device 200 form the mobile devices 120*a*-120*c*, the electronic device 200 depicted in FIG. 2 may include a fitness activity server input/output (I/O) 122. The personalized fitness system client 200 may further include a third-party integration I/O 204, a sensor I/O 206, and a user I/O 212. The electronic device 200 depicted in FIG. 2 further includes a time generator 208. The electronic device 200 depicted in FIG. 2 further includes memory 214, one or more processing units 216, and a display 210. Each of the components listed above may be coupled to each other by an electrical bus 290.

The fitness activity server input/output (I/O) 202 may be configured to transmit messages and/or other information to and receive messages and/or other information from fitness activity servers, for example, the fitness activity server 106 as referenced in FIG. 1 via the network 104. Transmitting the messages may include formatting data and values into a machine readable format and sending the message via a communication means. The communication means, as described above, may include any data communication means such as radio, digital network packet, fiber optic packet, or the like. Receiving the messages may include decoding data from the network 104, identifying one or more values included in the decoded data, and providing the values for further processing consistent with the features described herein, for example providing the decoded data or values to the display 210, the memory 214, or any other component of the electronic device 200. As described above, the fitness activity server I/O 202 may be configured for wired, wireless, or hybrid input/output.

In some embodiments, the fitness activity server I/O 202 may transmit information from the fitness activity server 106 of FIG. 1 comprising profile information, initial fitness information, desired target performance metrics, or other information relating to the monitoring or performance of the fitness program and the exercise regimen therein. For example, the user may input a name and other personal information as profile information via the user I/O 212, which may be communicated from the user I/O 212 to the fitness activity server I/O 122 via bus 290. In some embodiments, the processing unit 216 may modify or convert the information input via user I/O 212 before sending the information input to the fitness activity server I/O 202. Similarly, the sensor I/O 206 or the time generator 208 may be configured to generate information for transmission by the fitness activity server I/O 202. The information generated by each of these components will be described in more detail below.

As discussed above, the fitness activity server I/O 202 may be configured to receive information from the fitness activity server 106 of FIG. 1 comprising requests for information or information to be output to the user or to be used by one of the other components of the electronic device 200. For example, the fitness activity server I/O 202 may receive a request for information from the fitness activity server 106. The request for information may include a request for one or more of profile information, initial performance metrics, desired target performance metrics, exercise results, profile update information, or any other information that the fitness program system 105 may desire or need from a user or the electronic device 200. For example, the fitness program system 105 may send a request to the electronic device 200 via the fitness activity server I/O 202 requesting acknowledgement of the completion of a scheduled exercise regimen or requesting the user update or retest the force metric. Alternatively (or additionally), the fitness program system 105 may send information to the electronic device 200 via the fitness activity server I/O 202 for display to the user. For example, the fitness program system 105 may send information relating to a proposed exercise regimen that the fitness program system 105 generated based on inputs provided by the user to the fitness program system 105, such as number of repetitions (reps) of a specific exercise or specific target goals to reach for a specific exercise. The use of received information by each of the components of the electronic device 200 will be described in more detail below.

As discussed above, electronic device 200 shown in FIG. 2 includes the third party integration I/O 204. The third party integration I/O 204 may be configured to interact with third party devices, systems, or websites, such as social media websites, fitness program system partners or retailers, and the like. These interactions may include transmitting information to or receiving information from the third party devices, systems, or websites. For example, the third party integration I/O 204 may allow for interaction with social media websites or networks, computers, watches, media players, or other external electronic devices capable of displaying information to the user or communicating information related to the user's fitness program. In some embodiments, the interaction provided by the third party integration I/O 204 may allow for posting information to or receiving information from websites associated with the fitness programs or social media websites (for example, updating one's status, information about one's progress in the fitness program, metrics or other information relating to the fitness activities, or a friend list, etc.). The interactions via the third party integration I/O 204 may allow for comparisons of the user's progress to be made with other users' progress in similar fitness programs or having similar target performance metrics or may allow for the user to request assistance from another user or a trainer, etc. The third party integration I/O 204 may be configured for wired, wireless, or hybrid input/output.

In some embodiments, the information received by the third party integration I/O 204 may be communicated to one or more of the other components of the electronic device 200 via the bus 290. Alternatively, the information output by the third party integration I/O 204 may be sourced from one or more of the other components of the electronic device 200 via the bus 290. For example, when the third party integration I/O 204 receives information, for example, comparison information from a social media website, the received information may be communicated to the display 210 via the bus 290. In some embodiments, the received information may be first communicated from the third party integration I/O 204 to the one or more the processing units 216 for manipulation or formatting as necessary to be used by the other components of the electronic device 200. Similarly, information sourced from one or more other components of the electronic device 200 may be first communicated to the one or more processing units 216 before being communicated to the third party integration I/O 204 for outputting to third party devices, systems, or websites.

As discussed above, electronic device 200 shown FIG. 2 includes the sensor I/O 206. The sensor I/O 206 may be configured to interact with external sensors that may be used while performing the exercises of the exercise regimen. For example, the external sensors with which the sensor I/O 206 may interact may include sensors built into the fitness equipment (for example, the measurement equipment of a treadmill or an elliptical device). In some embodiments, the external sensors may be built into wearable fitness equipment, for example shoe sensors, glove sensors, or devices similar to heart rate monitors. The external sensors with which the sensor I/O 206 is configured to interact may be capable of communicating information with the sensor I/O 206 and detecting, monitoring, and communicating information relating to a current or a completed exercise regimen to the sensor I/O 206. In some embodiments, the sensors may include a GPS, a camera, an accelerometer, or a Bluetooth™ device such as a heart monitor, treadmill, elliptical trainer, stair machine, stationary hike, smart watch, and the like.

In some embodiments, the sensor I/O 206 may be configured to communicate information to the external sensors that may be used by the external sensors to be calibrated to the user. The communicated information may be acquired from information stored in the memory 214 or information received from the fitness program system 105 via the fitness activity server I/O 202 or received from a third party system via the third party integration I/O 204. For example, the sensor I/O 206 may communicate the user's weight or length of stride or any other information that may be used by the external sensors to properly calibrate to the user so as to be as accurate and useful as possible in generating measurements or monitoring the users exercises. In some embodiments, the sensor I/O 206 may be configured to receive measurements or other information gathered by the external sensors. The sensor I/O 206 may then share the received measurements or information with the appropriate components of the electronic device 200. In some embodiments, the received measurements or information may be first communicated to the one or more processing units 216 for manipulation or formatting before being communicated to the appropriate components of the electronic device 200. The third party integration I/O 204 may be configured for wired, wireless, or hybrid input/output.

For example, in some embodiments the sensor I/O 206 may be configured to communicate with external sensors to receive or input the initial user information. In some embodiments, the sensor I/O 206 may communicate with shoe sensors embedded in the user's shoe(s) to receive information to be used as the initial user information. In some embodiments, the sensor I/O 206 may receive information from the user's shoe sensors relating to the force generated by the foot/shoe against the floor. For example, when the user is performing a hex bar deadlift for the first time to determine the user's initial (or other) force metric, the shoe sensor may generate a force or similar input corresponding to the force applied by the foot/shoe on the ground. This input may correspond to the weight of the deadlift, and thus may be used to determine the force metric for the user. In some embodiments, the user may not perform a hex bar deadlift to determine the user's initial (or other) force metric. As described above, for the hex bar deadlift to utilize 90-95% of the user's skeletal muscle and thus be useful in determining the user's accurate force metric, the user should perform a hex bar deadlift of a weight that the user may only lift one or two times (one or two repetitions).

In some embodiments, the fitness program system 105 may be capable of determining the user's force metric from three different jumps using inputs or forces obtained via the shoe sensors communicating with the sensor I/O 206. For example, the user may be required to perform a squat jump, a split lunge/thrust jump, and a seated single, leg jump. During the performance of each jump, ground force may be sensed by a sensor such as a shoe sensor included in the user's shoe or a ground force mat. The sensing device may provide the sensed data via the sensor 206 for further processing. Similarly to the hex bar deadlift, for the three jumps to be effective to determine the user's force metric, the user must jump as high as possible for each of the three jumps. Each of the three, jumps may be described in more detail below.

As previously indicated, electronic device 200 shown in FIG. 2 includes the dine generator 208. The time generator 208 may be configured to generate one or more timing sequences that may be used by the electronic device to monitor and track the user's progress during the exercise regimens of the fitness program. For example, the time generator 208 may be configured to generate a timer for use in measuring elapsed time during a running exercise or for use in stretching, etc. In some embodiments, the time generator 208 may be configured to track or monitor a current time or date so as to provide timely and relevant updates regarding the user's progress through the fitness program. For example, the time generator 208 may allow the electronic device 200 to update the fitness program system 105 of FIG. 1 when the user completes the exercise regimen scheduled for a particular date on, before, or after the target date so that so that continuous communications are not required between the electronic device 200 and the fitness program system 105. In some embodiments, one or more of the other components of the electronic device 200 may use a time or timer generated by the time generator 208 in operation.

The display 210 of the electronic device 200 may be configured to display information to the user. The display 210 may be configured to receive information from one or more of the other components of the electronic device 200. In some embodiments, the display 210 may include at least one of an LCD display, an LED display, a MEMS display, an e-ink display, or a display of any other display technology. In some embodiments, the display 210 may include other audio or visual communication modes, for example a speaker, a vibrating indicator, or a text display.

The user I/O 212 of the electronic device 200 may be configured to receive inputs from the user or output information to the user separate or in addition to the information output to the user via the display 210. For example, the user I/O 212 may include touchscreen display or a physical keyboard. In some embodiments, the electronic device 200 may include one or more physical buttons or rotary selectors which may be included in the user I/O 212. In some embodiments, the user I/O may be configured for wired, wireless, or hybrid wired/wireless communication with the electronic device 200.

As previously indicated, the electronic device 200 may include the memory 214. The memory 214 may be configured to store and retrieve information. The stored information may be related to one or more of the user, the user's fitness program, the user's exercise regimen, a user's postural regimen, or any other information that may be relevant to the user's participation in the fitness program. In some embodiments, where the electronic device 200 is configured to perform other functions besides those relating directly to the fitness program (for example, where the electronic device 200 is a smart phone capable of being used in conjunction with the fitness program as described above), the memory may be configured to store information that is not relevant to the fitness program. The memory 214 may include one or a combination of memory devices, including Random Access Memory, nonvolatile, backup memory (for example, programmable or Flash memories, read-only memories, etc.), networked memory (for example, cloud storage).

In an embodiment, as described above, where the electronic device 200 may include the functionality and/or components of the fitness program system 105, the memory 214 may include the force/metric data store 108, the exercise data store 110, and/or the fitness program data store 112.

Accordingly, the memory 214 may be used to generate, monitor, and modify fitness programs for the user and may be used to store the generated fitness programs. Any information that may be stored by the fitness program system 105 in any one of the databases 108, 110, and 112 may be stored by the memory 214 when the functionality of the fitness program system 105 is integrated into the electronic device 200. The processing unit(s) 216 of the electronic device 200 may be configured to perform the processing functions of the fitness program system 105, for example the manipulation of inputs from the users 102a-102c and the generation of the fitness program and the manipulation of the user's force metric, performance metrics, and any other data manipulation or development of any routines or anything related to the generated fitness program. The $3^{rd}$ party integration I/O 204, the sensor I/O 206, the time generator 208, the display 210, and the user I/O 212 may function as described above.

The one or more processing units 216 of the electronic device 200 may be configured to manipulate or convert information used by any of the other components of the electronic device 200. For example, the one or more processing units may be configured to receive information received by the sensor I/O 206 or the third party integration I/O 204 and format it for display on the display 210. For example, this may comprise performing various calculations or conversions on the received information, for example converting a number of steps into a distance traveled or converting a time in seconds to a format of minutes and seconds. In some embodiments, the one or more processing units 216 are configured to obtain instructions and data via a bus 290 from the memory 214. The processing units 216 may be implemented as a programmable logic device that performs instruction, logic, and mathematical processing, and may be representative of one or more CPUs.

In some embodiments, the one or more processing units 216 may include an individual or dedicated processing unit for one or more of the other components of the electronic device 200. For example, the fitness activity server I/O 122 may include its own processing unit, while the third party integration I/O 204 and the sensor I/O 206 also have their own processing units, respectively. Similarly, the time generator 208 and the user I/O 212 may include individual, dedicated processing units. The display 210 and the memory 214 may not include their own processing units, but may instead benefit from the processing units of the other components of the electronic display 200.

The elements of the client 200 are coupled by the bus 290. The bus 290 is configured to allow the elements to exchange data and/or power. In some implementations, parallel busses may be included, one for data and one for power.

Though not shown in FIG. 2, the electronic device 200 may include a fitness program generator. The fitness program generator may include one or more of a workout or an exercise regimen generator, a postural regimen generator, and a real-time coaching generator. The fitness program generator may be configured to receive the inputs described above as received by the fitness program system 105 and generate, monitor, and modify fitness programs personalized to the user. When integrated into the electronic device 200, the fitness program generator may be configured to display information on the display 210 and receive inputs from or transmit outputs to the various I/O of the electronic device 200 (for example, the third party integration I/O 204, the sensor I/O 206, and the user 212). As discussed above, when the fitness program system 105 is integrated into the electronic device 200 (for example, into a fitness program generator), the electronic device 200 may not include the fitness activity server I/O 202, but may rather include a network I/O. The fitness program generator may be configured to receive inputs via user inputs (for example, height, weight), via sensors included in the device (for example, GPS, camera, accelerometer), via sensors in data communication with the device (for example, Bluetooth™ heart monitor), or via the network 104 from service providers for the device (for example, cellular provider, network provider). The fitness program generator uses these inputs to generate, modify, and monitor the user's fitness program through the use of exercise regimen, postural regimen, and real-time coaching. The fitness program generator may be further configured to present the various received or generated information to the user via the display 210.

Some embodiments of the electronic device 200 may include a physical activity monitor. The physical activity monitor may be configured to receive activity information such a cardiovascular activity type, duration, and intensity. The information may be provided via user inputs (for example, height, weight), via sensors included in the device (for example, GPS, camera, accelerometer), or via sensors in data communication with the device (for example, Bluetooth™ heart monitor). In some implementations, the physical activity monitor may be configured to access a database, for example, a database of activity types used to determine the number of calories burned by an identified activity. The databases accessed by the physical activity monitor may be stored locally in the memory 214 or externally (accessible via the network I/O or the third party integration I/O 204). The physical activity monitor, in some implementations, is configured to provide real-time coaching during a workout. For example, if the physical activity monitor identifies a period of activity which exceeds a predetermined threshold of time or is under the predetermined threshold of time, the physical activity monitor may be configured to display a message to the user via the display 210 to indicate to the user of the detected situation. In some embodiments, the physical activity monitor may be configured to communicate with the fitness program generator to have the fitness program generator modify the fitness program in light of the user's actual progress.

While multiple discrete elements are shown in FIG. 2, it will be appreciated that, in some implementations, the elements may be commonly implemented such as a combination of the fitness activity server I/O 202, the third party integration I/O 204, the sensor I/O 206, and the user I/O 212 or the time generator 208 and the one or more processing units 216.

As described above, the electronic device 200 may be configured to run an app, and the app may be capable of interacting with the various components of the electronic device 200. The app may be any software program or similar collection of commands with or without a graphical user interface. The software application may be configured to operate independently and in addition to an operating system on the electronic device 200 or may be configured to operate on the electronic device 200 dedicated to the software application such that the electronic device 200 is not used for any other purpose. As discussed above, the app operating on the electronic device 200 may be configured to interact with the fitness program system 105 as depicted in FIG. 1 via the various components of the electronic device 200 and the network 104. In some embodiments, the software application operating on the electronic device 200 may include the functionality of the fitness program system 105 as integrated into the electronic device 200. Accordingly, the software application may be configured to generate, modify, and monitor fitness programs generated for any user associated with the software application and the electronic device 200. As described herein, the software application may be configured to provide the user with accessibility to the features of the fitness program system.

Figure 3:
FIG. 3 shows an example of an activity that may induce the generation of the protein in a user's body, in accordance with an exemplary embodiment.

FIG. 3 shows an example of an activity that may induce the generation of the protein in a user's body, in accordance with an exemplary embodiment. The fitness program generated by the fitness program may begin with an activity that utilizes over 90% of the user's skeletal muscle. As shown in FIG. 3A, an example of this activity may include a maximum hex bar dead lift, where the user performing the hex bar dead lift performs at his/her maximum capability. In some embodiments, performing the exercise that utilizes nearly all of the user's skeletal muscle (more than 90% of the user's skeletal muscle) may induce the body to generate and release a CRTC2 protein into the user's bloodstream. Such exertion may cause the body to recruit Type 2b motors units to adapt to the stress placed on the body under the maximum effort. Additionally, lactate transporters may be recruited to up-regulate toxins released by the muscles. In some embodiments, the CRTC2 protein may be induced through other activities, such as being chased by a bear or being injected into the user. The described features provide personalized schedules which include activities that are scheduled such that the optimal levels of the protein may be induced or introduced into the body by any other means. The existence of the CRTC2 protein in the user's body during exercises of the fitness program may enhance maximal exercise capacity by 103% when compared to performance of the same exercises without the CRTC2 protein in the user's body are present for a subsequent workout.

In some embodiments, a development of the user's force metric may be based on an exercise that utilizes over 90% of the user's skeletal muscle. For example, the maximum hex bar dead lift weight the user lifts may be used to generate the user's force metric using Equation 1 below.

$$\text{Force Metric} = \text{Maximum Hex Bar Dead Lift/User's Weight}/(V\#)*25, \quad (1)$$

where the V # is based on the height of the user. If the user is under 5'9" then the V # is 0.9. If the user is between 5'9" and 6'X" then V # is 1.1. If the user is greater than 6'X" then V # is 1.3. The user's force metric, as described herein, may be used to calculate and determine the performance metrics of the user. For example, the user's speed can be determined based on the user's force metric, as can be the user's power, the user's vertical jump height, or any other physical performance metric of the user that may be related to the user's strength or force generation capability.

The activity that utilizes over 90% of the user's skeletal muscle (for example the hex bar deadlift) may invoke the central nervous system of the user, causing the release of the CRTC2 protein described above. However, for a user to fully benefit from a scheduled workout or activity, the user's central nervous system should be close to its original (or unstressed) state. For example, in some embodiments, when the user performs the initial exercises to test the initial fitness metrics, the user's central nervous system may be at 100% capacity. Thus, when the initial exercise is a hex bar deadlift, the maximum weight that the user can lift for a single repetition may represent the user's central nervous system capabilities at 100% capacity. To fully benefit from future workouts and scheduled exercises, the user's central nervous system should be within 95% of the original test, meaning the maximum weight the user can lift for a single repetition for the hex bar deadlift should be within 95% of the initial maximum weight lifted. In some embodiments, the unstressed state may be determined to be within 90 or 85% of the original test. In some embodiments, the unstressed threshold may be determined to be within any other percent of the original test. If the user's central nervous system is within the prescribed threshold of its unstressed state, then the fitness program may "unlock" the remaining exercises or activities for the user to perform. For example, if the user's initial or most recent hex bar deadlift weight was 500 pounds and the user is capable of lifting 495 pounds at the beginning of a workout, then the fitness program may unlock the remaining exercises having determined that the user's central nervous system and body have properly recovered from the previous workout or are otherwise in proper condition to benefit from the day's scheduled workout.

If the user's central nervous system is not within the prescribed threshold, then the fitness program may remain "locked" as having determined to not be able to benefit from the workout, thus preventing the user from performing the scheduled activities until the fitness program determines the user is in a condition to benefit from the workout. For example, if the user's initial or most recent hex bar deadlift weight was 500 pounds but the user is unable to perform a single lift at 450 pounds, then the fitness program may lock the remaining scheduled exercises for the day until the user's body and central nervous system are in condition to fully benefit from the scheduled exercises. The locking and unlocking features will be described in further detail below.

FIGS. 4-13 illustrate screenshots of an app that may operate on the mobile device 120a-120c for the users 102a-102c of FIG. 1. As described below, the various screenshots of the app may display information generated by one of the fitness program system 105 or the app itself, and may request input from the user for use by the fitness program system 105 or the app itself. In some embodiments, any of the functions described below in relation to FIGS. 4-13 as being performed by the app may be performed by the fitness program system 105 using communications via the network 104 of the FIG. 1 described above. In some embodiments, any of the functions described below in relation to FIGS. 4-13 as being performed by the fitness program system 105 may be performed by the app when the mobile device 120a-120c includes the various components and information included within the fitness program system 105 described above in FIG. 1. Thus, functions attributed to one of the app or the fitness program or fitness program system 105 may be performed by any of the app, the fitness program, or the fitness program system 105. The app and the mobile device 120, as described herein, may be configured to interface with various sensors and/or other input means to receive information regarding the user during exercise routines or during periods when the user is inputting information. As described herein, the app and/or the fitness program system 105 may receive the inputs and use them to monitor the user's progress and adapt, such as via an update, the user's fitness program based on the user's progress and inputs. Thus, the fitness program system 105 and the software application may act as a virtual personal trainer capable of personalizing the fitness program to the requirements of the user and capable of providing guaranteed and predictable results. In some embodiments, the fitness program system 105 and/or the software application may be configured to determine a user's time to fatigue or other fitness information that may be useful in generating the personalized fitness program or providing training information.

Figure 4:
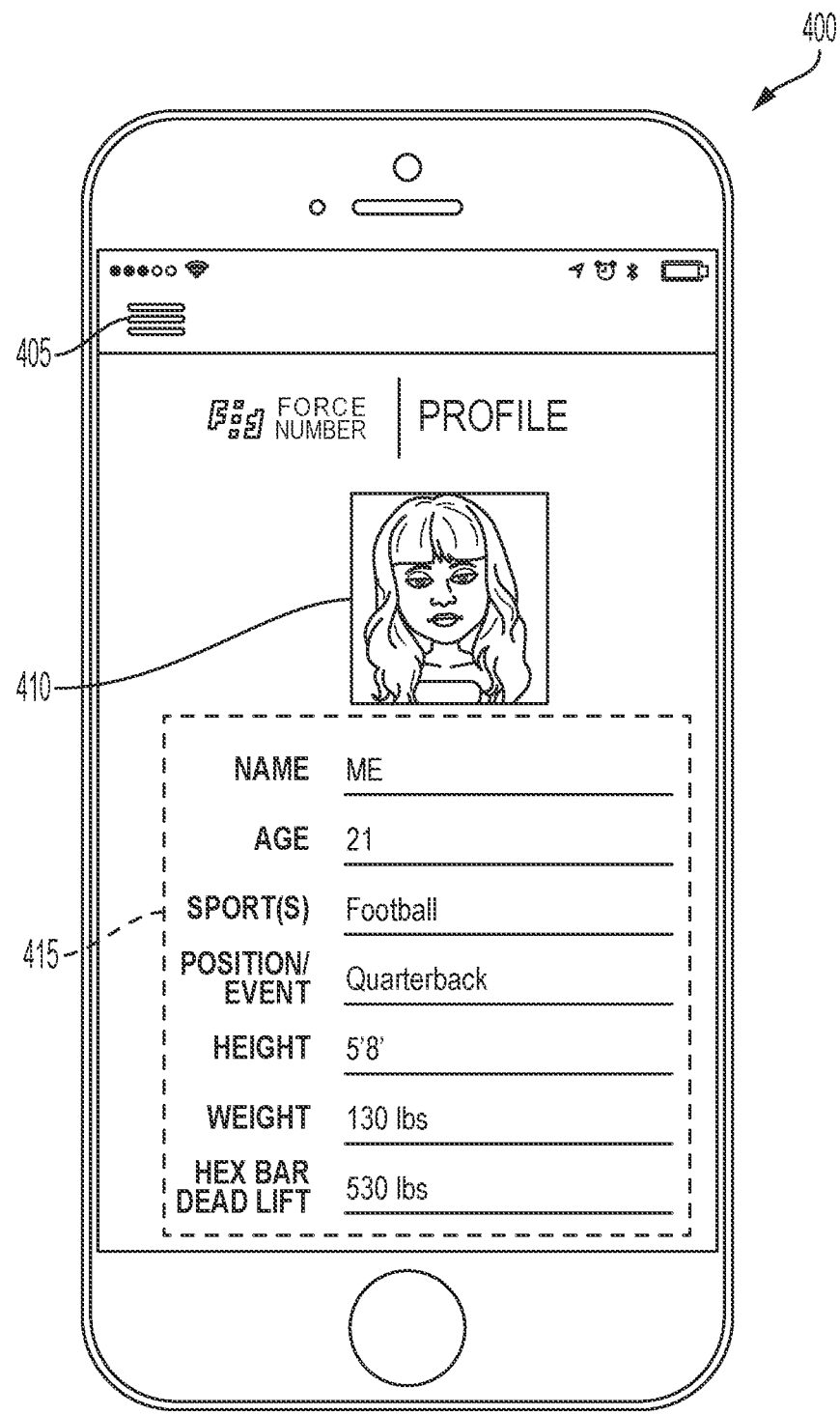
FIG. 4 shows an example of a screenshot of a user profile screen of an application that may be run on the device of FIG. 2, in accordance with an exemplary embodiment.

FIG. 4 shows an example of a screenshot of a user profile screen 400 of an app that may be run on the device of FIG. 2, in accordance with an exemplary embodiment. The user profile screen, as indicated in FIG. 4, may include personal information regarding a current user of the app. The profile screen may include a menu button 405, a profile picture 410, and a user profile information fields 415.

Though not shown in detail in this figure, the menu button 405 may toggle the activation or display of a menu on the user profile screen 400. When displayed, the menu may provide the user with controls for switching between other user profiles that may exist in the app. The menu may also provide access to other menu options, for example, options to edit any field of the user profile information fields 415 or the profile picture 410 or navigation controls to navigate to other screens of the app. The profile picture 410 may include any picture or photo as selected by the user. The profile picture 410 may be shared with other devices or social media or other websites if so desired by the user. The user profile information fields 415 may include the fields of personal information about the user as stored by the software application. The user profile information fields 415 include a name field, an age field, a sport field, a position or event field, a height field, a weight field, and a hex bar deadlift field. Additional fields (for example, fields associated with inputs received from external sensors, gender, etc.), fewer fields, or alternative fields may be included in the user profile information fields 415, though not shown as such in FIG. 4. As described above, the hex bar deadlift field may be measured by external sensors, for example shoe sensors. In some embodiments, the hex bar deadlift field may be replaced or supplemented by fields associated with the jump heights or forces exerted as measured by the shoe sensors in relation to the squat jump, split lunge/thrust jump, and the seated single leg jump.

The user profile information fields 415 and the profile picture 410 may be generated or selected when the user first requests that the fitness program be generated. In some embodiments, the user profile information fields 415 of the user profile screen 400 may be based on the initial information provided by the user. In some embodiments, the fields of the user profile information fields 415 may be predetermined or selected by the user regardless of the initial information that the user provides. In some embodiments, when one of the fields of the user profile information fields 415 is blank, the field may not be shown, while in other embodiments, blank fields may be shown on the user profile screen 400. Some of the fields (for example the sport and position or event fields) may be configured to accept multiple values. For example, the user could list in the sports field "football" and "soccer" or any other combination of sports as desired by the user. Similarly, the position or event field could contain multiple positions or events, for example, "goalie" and "striker" if the selected sport(s) includes soccer. As described above, the values indicated on the user profile screen 400 may be used by the software application in generating, monitoring, or modifying the user's fitness program. In some embodiments, the menu may provide the user with the option of toggling between standard or metric values for the user profile information fields 415 or may provide the user the ability to toggle the use of external sensors for automatic feedback with the fitness program (for example, shoe sensors, clothing sensors, or any other sensor that may be associated with a fitness activity).

Figure 5B:
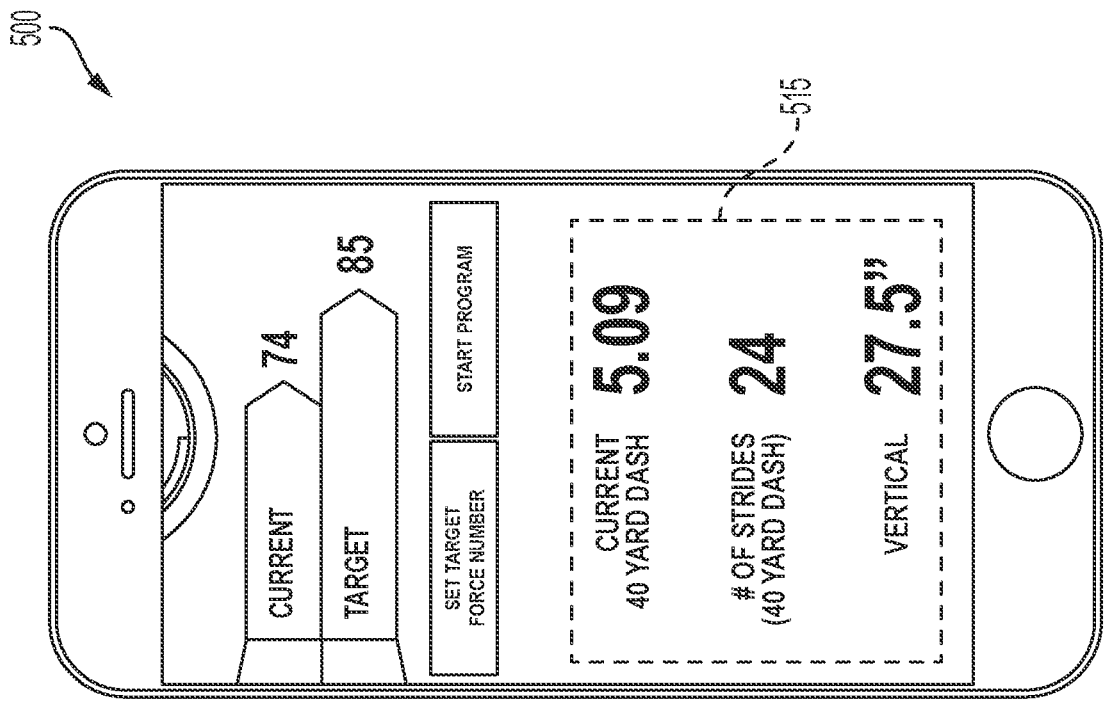
FIGS. 5A and 5B show an example of a screenshot of an initialization screen of the software application that may be active on the device of FIG. 2, in accordance with an exemplary embodiment.
Figure 5A:
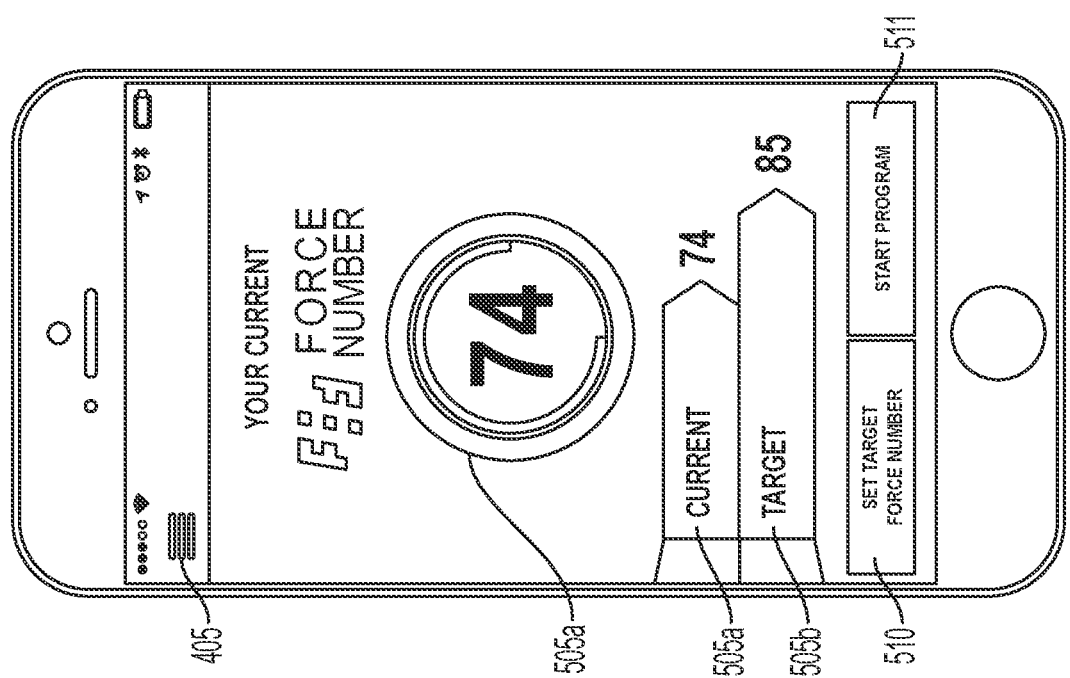

FIGS. 5A and 5B show an example of a screenshot of an initialization screen 500 of the software application that may be active on the electronic device 200 of FIG. 2, in accordance with an exemplary embodiment. The initialization screen 500 presents an overview of scrollable information (meaning the screen can scroll in at least one direction to display more information without navigating to an alternate screen) to the user and provides some general information to the user that may be pertinent to the fitness program. In some embodiments, the screens may not be scrollable. The initialization screen 500 includes a menu button 405, a current force metric 505a represented by two indicators, a bar graph-type indicator and a pie chart-type indicator. The initialization screen 500 also includes a target force metric 505b represented by a single bar graph-type indicator. The initialization screen 500 further includes two "soft" keys: a "Set Target Force Metric" soft key 510 and a "Start Program" soft key 511. The two soft keys 510 and 511 may allow the user to interact with the software application operating on the node device. The initialization screen 500 may further include initial or current performance metrics field 515.

As described above in reference to FIG. 4, the menu button 405 may toggle the display of the menu on the screen. The menu may provide the user with options to change the values of any field of the performance metric fields 515 or navigate to other screens of the software application. In some embodiments, the menu may provide the user with options to activate or deactivate external sensors, for example shoe sensors in the user's shoes. Activating the external sensors may require the user to pair or authenticate the desired sensors with the fitness program to ensure that the proper external sensors are being connected to the fitness program. In some embodiments, the pairing or authenticating of the external sensors with the fitness program may require the user to actively confirm that the fitness program is connecting to the correct external sensors. For example, the fitness program may display identifying information for the detected external sensors and request that the user confirm that the displayed sensor(s) should be connected and determined to be secure. In some embodiments, the fitness program may request the user place the external sensors in a pairing or coupling mode where identifying information is communicated between the fitness program and the external sensor for confirmation by the user. In some embodiments, the fitness program may request the user activate a pairing mode in both the fitness program and the external sensor that automatically pairs any devices detected as being within the pairing mode. In some embodiments, the user may be able to save and/or name paired external sensors so that they are automatically connected as secure and/or trusted sensors when detected by the fitness program in the future. When the external sensors are activated in the menu options, the fitness program may receive and utilize inputs from the external sensors. When the external sensors are deactivated in the menu options, the external sensors may be ignored by the fitness program.

The current and target force metrics 505a and 505b may be configured to provide a visual indicator of the current and target values of the users force metrics 505a and 505b respectively. The performance metrics field 515 may be configured to indicate initial measured performance metrics or current measured performance metrics. The soft key 510 may allow the user to change the target force metric as indicated by target force metric 505b. Pressing the soft key 510 may open a window allowing for input of a numerical value. In some embodiments, the user may be allowed to enter the target force metric directly. In some other embodiments, the user may enter target performance metrics and the software application may calculate the target force metric for display on the initialization screen 500 as target force metric 505b based on the user entered target performance metrics. The soft key 511 may allow the user to toggle starting and stopping of the fitness program generated above.

FIG. 6 shows an example of two screenshots of two postural evaluation screens 600a and 600b of the software application that may be active on the device of FIG. 2, in accordance with an exemplary embodiment. The postural evaluation screen 600a depicts a side view of the user's posture. The postural evaluation screen 600a depicts a side view image of the user's body with indicators of both a correct posture 605a and the user's (incorrect) posture 605b as indicated by various joints or body part locations with respect to each other. Similarly, postural evaluation screen 600b depicts a front view of the user's posture. The postural evaluation screen 600b depicts a front view image of the user's body with indicators of both a correct posture 610a/615a and the user's incorrect posture 610b/615b indicated at different locations of the user's body. The posture indicated by lines 610a and 610b is measured at the user's waist, while the posture indicated by lines 615a and 615b is measured at the user's shoulders. Additionally, the postural evaluation screen 600b depicts a degree of imbalance as measured at the user's waist and at the user's shoulders between the "correct posture" and the "user's posture," for example a 20-degree imbalance between lines 610a and 610b (at the hips) and a 22-degree imbalance between lines 615a-615b (at the shoulders). The posture screens or portions of the software application may be used to help the user prevent injury or improve form, which may result in further improvements in the force produced by the user.

At the top of the postural evaluation screens 600a and 600b are navigation buttons 620a. The navigation buttons 620a may include two individual buttons, one labeled "Screening" and the other labeled "Home." At the bottom of the postural evaluation screens 600a and 600b are navigation buttons 620b. The navigation buttons 620b may include four individual buttons labeled "Results," "Front View," "Side View," and "Next." The "Screening" navigation button depicted may take the user to the app's postural screening screen (not shown in these figures). The postural screening screen may allow the user to upload or capture a picture of the user's body in an indicated view (front, side, back, etc.). The "Home" navigation button may allow the user to navigate to the app's home screen. In some embodiments, the app's home screen may include the initialization screen 500 shown in FIG. 5 or the user profile screen 400 shown in FIG. 4. In some embodiments, the app's home screen may include another screen not shown in these figures. The "Results" navigation button of the navigation buttons 620b may allow the user to navigate to results postural evaluation results screens of the software application, for example postural evaluation screens 600a and 600b. In some embodiments, the "Results" navigation button may navigate the user to another screen not shown in these figures that shows results of the postural evaluation of the user. The "Front View" navigation button may allow the user to navigate to the postural evaluation screen 600b showing the front view of the user's body, while the "Side View" navigation button may allow the user to navigate to the postural evaluation screen 600a showing the side view of the user's body. The "Next" navigation button may allow the user to navigate to the next postural evaluation screen (for example, navigate between the front view and side view screens) or may allow the user to navigate to additional navigation buttons.

Figure 7:
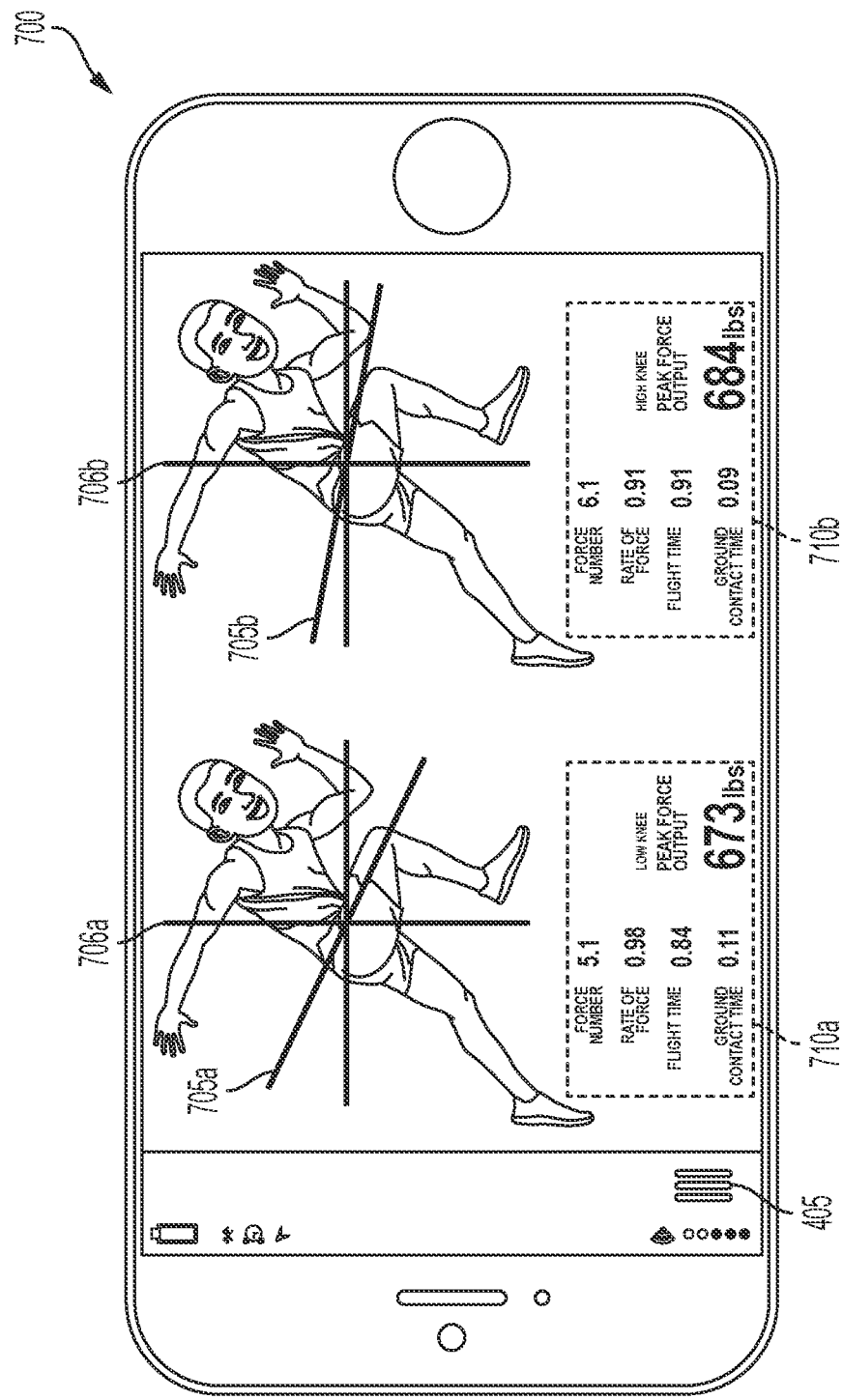
FIG. 7 shows an example of a screenshot of a real time coaching screen of the software application that may be active on the device of FIG. 2, in accordance with an exemplary embodiment.

FIG. 7 shows an example of a screenshot of a real-time coaching screen 700 of the software application that may be active on the device of FIG. 2, in accordance with an exemplary embodiment. The real-time coaching screen 700 includes a menu button 405, as described above in relation to FIG. 4, and depicts two images of the user's body along with two sets of axes 706a and 706b, two lines of incidence 705a and 705b, one on each of the sets of axes 706a and 706b, and two sets of performance metrics 710a and 710b. The real-time coaching screen 700 may present information generated and used by the real-time coaching function of the fitness program.

The real-time coaching function may be a function of the fitness program or software application running on the electronic device 200. The real-time coaching function may allow the fitness program to provide real-time guidance and support to the user while the user is using the app. For example, the user may use the real-time coaching function to monitor the user's progress through an exercise regimen. In some embodiments, the coaching info may not be real-time and instead may be provided by the fitness program system 105 based on a trainer's evaluation of the user's progress. In some embodiments, the coaching information may be generated based on one or more algorithms monitoring the information of the user's progress in one or more exercises of the fitness program. For example, the coaching information for the user may be based on the performance of the user during a running exercise and based on the one or more algorithms. The one or more algorithms may be generated and modified based on data sampled and analyzed over years of collection and testing of various users. In some embodiments, the real-time coaching function may capture an image of the user's body and evaluate the user's form, etc., in the exercise regimen to determine if any recommendations should be made to the user to improve the user's performance in or results from the exercise regimen being performed. In some embodiments, the real-time coaching function may monitor data received from the external sensors (for example the shoe sensors discussed above) to determine whether recommendations can be made to the user to improve the user's performance or results. In some embodiments, the real-time coaching function may receive data from external sensors, data entered by the user, or data captured by one or more internal sensors, including a camera or audio sensor.

Regardless of how the real-time coaching function obtains the relevant information, the real-time coaching screen 700 shown in FIG. 7 may display the user's body (or a representation thereof) on the axes 706a This display of the user's body may be indicative of the user's body before the real-time coaching function provides recommendations to the user, while the user's body on the axes 706b may represent the results predicted to be attainable or having been measured as being attained after the recommendations to the user from the real-time coaching function. The performance metrics 710a show the user's performance without the recommendations, while the performance metrics 710b show the user's projected performance with the recommendations implemented. The performance metrics 710a may include the user's force metric, the user's rate of force, the user's flight time, the user's ground contact time, and the peak force output from the stride shown on the axes 706, all measured before the recommendation. The performance metrics 710b may show the projected performance metrics if the user follows the real-time coaching recommendations, or the actual performance metrics if the user did follow the real-time coaching recommendations.

As shown in FIG. 7, the real-time coaching screen 700 of the software application provides the user with ample information to both determine whether or not to follow the real-time coaching recommendation and understand the real-time coaching recommendation that is presented by the software application. For example, the images displayed on axes 706b may provide sufficient instruction to the user to indicate what changes the user should make to attain the projected performance metrics. As shown in FIG. 7, the user's body on axes 706b shows that if the user lifts his front leg higher in the stride, the user will increase his force metric, flight time, and peak force output while reducing the user's rate of force and ground contact time. In some embodiments, the image on the axes 706b may act as a link to additional instructions, video, or directions to the user to attain the recommended form. In some embodiments, the fitness program system 105 or the electronic device 200 operating the software application may be configured to receive an input from the external sensors or internal I/O indicating the user's current actions and providing information regarding the user's metrics. For example, the peripheral electronic device 122 being a shoe having the internal shoe sensors (for example, located in one or more of the midfoot, heel, toes, arch, etc.) to measure forces exerted by the foot and impacts felt by the foot may be able to provide the time between when the user's foot leaves the ground and impacts the ground while the user is taking steps. Additionally, the peripheral device 122 shoe may be configured to measure a height of the shoe. This information may be communicated to the mobile device 120 (corresponding to the electronic device 200), which may be configured to determine the user's current movements or communicate the received information to the fitness program system 105 that may determine the user's current movements or range of motion from the received information. The mobile device 120 or the fitness program system 105 may then generate recommendations to improve the user's movements or forces generated. The recommendations may take into account the user's current information compared with identified improved metrics and initial information (for example, the user's height or length of legs, etc.), and tell the user what actions are needed to generate the improved metrics. Thus, the mobile device 120 or the fitness program system 105 may instruct the user to raise his knee a few inches to generate additional peak force output over the original movements. Though not shown on this screen, the real-time coaching screen 700 may be configured to provide real-time coaching for various activities or sports (for example, running, throwing, kicking, swinging, swimming, cycling, etc.). In some embodiments, the real-time coaching screen 700 may provide information or recommendations in response to issues identified by the user, for example specific pains while exercising or specific difficulties during the exercise regimen. The real-time coaching information displayed via the user's body on the different axes may only be representative of the recommendations and may not be exact with regards to the steps to be performed.

Figure 8:
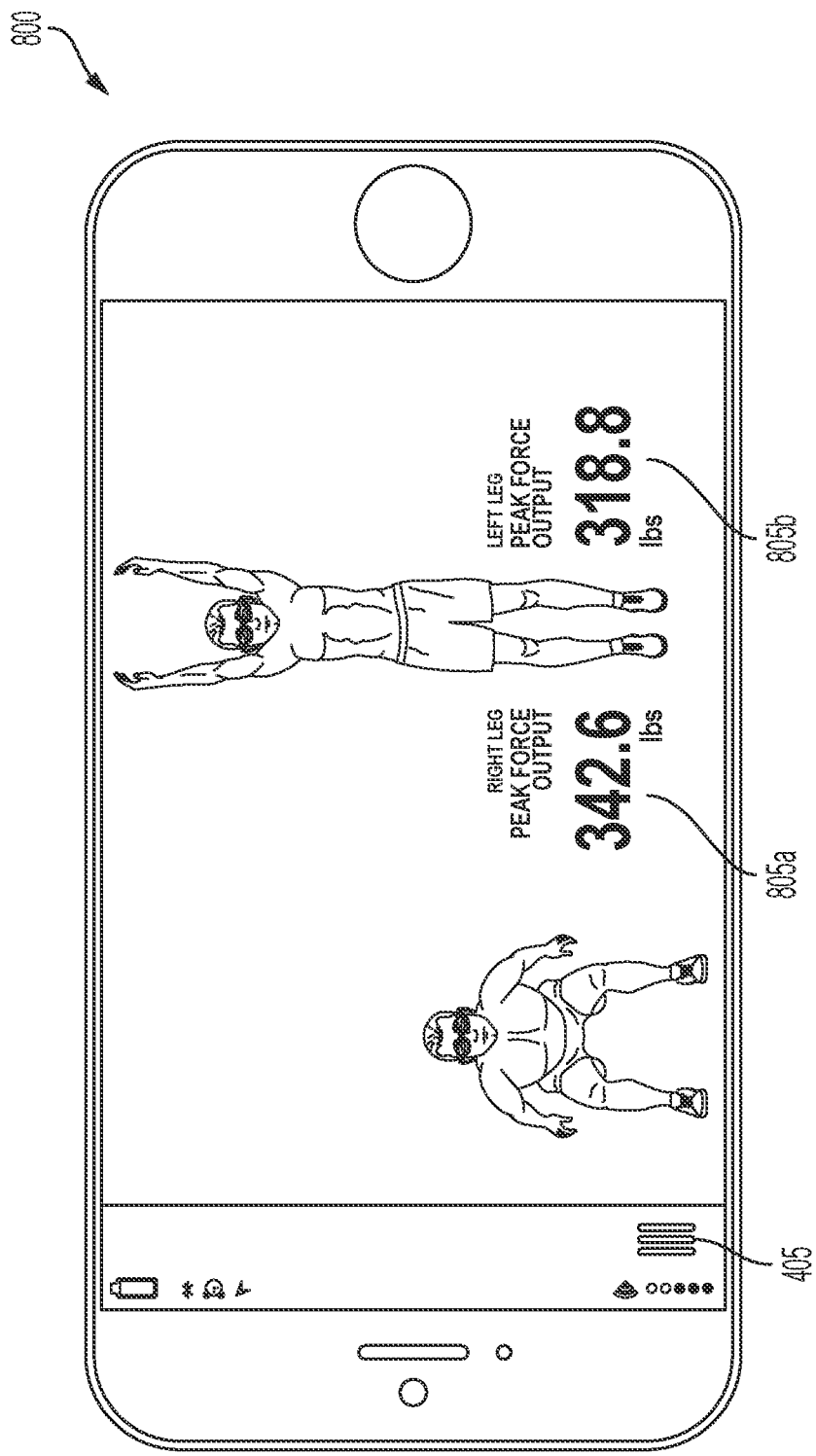
FIG. 8 shows an example of a screenshot of a real time data screen of the software application that may be active on the device of FIG. 2, in accordance with an exemplary embodiment.

FIG. 8 shows an example of a screenshot of a real time data screen 800 of the software application that may be active on the device of FIG. 2, in accordance with an exemplary embodiment. The real-time data screen 800 includes a menu button 405, as described above in relation to FIG. 4, and depicts two images of the user's body along with two data points 805a and 805b.

The real-time data screen 800 may be configured to display real-time data as obtained by the app. For example, the real-time data may be obtained by the electronic device 200 communications with external sensors, for example sensors in the user's shoes or clothing. Alternatively, in some embodiments the real-time data may be obtained by the electronic device 200 capturing of an image of the user and analyzing the image or receiving data input by the user in real-time. The real-time data screen 800 may be useful in the fitness program's development of the real-time coaching screen 700, as discussed above in relation to FIG. 7, or in the modification, tracking, or monitoring of the fitness program.

The information and images shown on the real-time data screen 800 may represent any information related to the fitness program and are not limited to those shown in FIG. 8. In some embodiments, the real-time data screen 800 may display the forces generated by the user in any of the three jumps that may be used to determine the user's force metric: the squat jump (shown in FIG. 8), the split lunge/thrust jump, and the seated single leg jump. In some embodiments, the real-time data screen 800 for the squat jump may include the power and quantity of force generated by the user during the jump and be able to determine the forces generated by each leg (as shown in FIG. 8). Thus, the squat jump may be allow the fitness program to determine any left/right imbalances in the user's legs. The split lunge/thrust jump may provide the fitness program with the single leg power and quantity of force generated by the back side (muscles on the back side of the leg) of the user's legs. Similarly, the seated single leg jump may test the power or force generated by the front side (muscles on the front side of the leg) of the user's legs. The split lunge/thrust jump and the seated single leg jump may allow the fitness program to determine any front/back imbalances in the user's legs.

As shown in FIG. 8, the data point 805a shown may represent the force generated by the user's right leg, while the data point 805b may represent the force generated by the user's left leg. As can be seen, the user's legs each output different forces (342.6 pounds of peak force from the right leg and 318.8 pounds of peak force from the left leg) for an activity that may be expected to generate the same output from each leg (for example, a vertical jump). Accordingly, the app may identify the discrepancy between the force outputs of each leg and indicate the discrepancy to the user.

In some embodiments, based on the identified discrepancy, the app may automatically use the real-time coaching screen 700 to present recommendations to the user to reduce the discrepancy between the force outputs of the legs, for example, generating stretches or exercises to bring the force outputs of the left and right legs into closer symmetry. In some embodiments, the fitness program system may update the generated fitness program to accommodate the recommended stretches or exercises and so as to schedule the new recommended activities into the user's fitness program. In some embodiments, the app may request the user's input as to whether or not the user wants the fitness program to generate a recommendation to reduce the discrepancy or ignore the discrepancy. In some embodiments, when the user incorporates exercises or activities to reduce any front/back or left/right or any other imbalances, the real-time data screen 800 may include information regarding the scheduled activities or exercises that will improve the detected imbalance.

While the exemplary embodiment shown in FIG. 8 depicts the user performing a jump with data pertaining to the forces generated by each leg, other embodiments may display a height of each leg in a jump, a stride length taken by each leg during a run, a force exerted by each arm in a weight lift or swim stroke, or a force exerted by each arm in a swing, or any other physical metrics. Other embodiments may display real-dine data received by the electronic device 200 from external sensors, the user, or the electronic device 200 in any fitness activity the user may perform. In some embodiments, the user may use the real-time data screen 800 and the real-time coaching screen 700 for physical activities that are not part of the fitness program in which the user may be participating.

Figure 9:
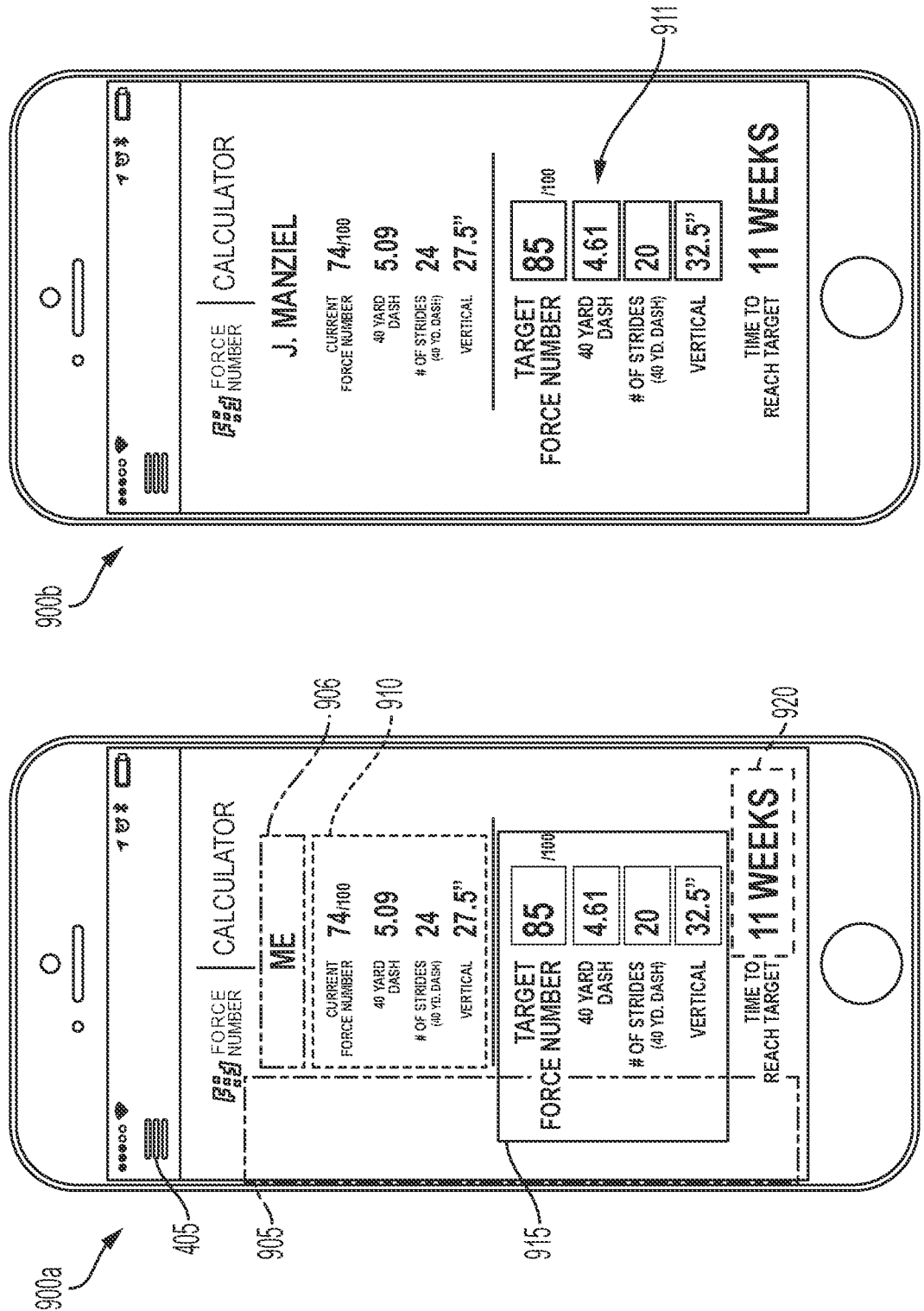
FIG. 9 shows an example of a screenshot of a calculator or target calculation screen of the software application that may be active on the device of FIG. 2, in accordance with an exemplary embodiment.

FIG. 9 shows an example of a screenshot of a calculator (or target calculation) screen 900 of the software application that may be active on the device of FIG. 2, in accordance with an exemplary embodiment. The calculator screen 900 includes the menu button 405 as described above in relation to FIG. 4 and various fields or indicators. The included fields and indicators include a sport indicator 905, a user name field 906, a current performance metrics fields 910, a target performance metrics fields 915, and a target time field 920. Additionally, the calculator screen includes a screen identifier "Calculator" so that the user knows what screen he is currently viewing. In some embodiments, the calculator screen may be identified with any other identifier describing the function of the screen.

The sport indicator 905 may correspond to the sport information entered by the user in reference to the user profile screen 400 in the user profile information fields 415. In embodiments where the user entered more than one sport into the user profile information fields 415, multiple calculator screens 900 may be generated by the software application, for example one for each sport or calculator screens 900 with information from multiple sports combined on the single screen (for example, a scrollable screen, or a screen with various tabs, etc.). Multiple calculator screens 900 may be used because each sport or position or event may have different performance metrics that are important to identify and improve. For example, football, as shown in FIG. 9, may focus on a 40 yard dash time, number of strides taken in the 40 yard dash, and a vertical jump height, while baseball may focus on a 60 yard dash time, a maximum throwing velocity, and a vertical jump height, and running may focus on a 6 minute vV02MAX test, a 6 minute distance test, and a marathon time. In some embodiments, other sports (e.g., volleyball, track and field events, distance running, surfing, paddle boarding, lacrosse, baseball, basketball, ice hockey, field hockey, polo, gymnastics, golf, jai-alai, tennis, curling, soccer, racquet ball, squash, cycling, sport fishing, Highland gaming, martial arts, football, water skiing, snow skiing, snow boarding, wrestling, swimming, figure skating, or other physical activity) may focus on the same or other performance metrics, or the sports identified above may focus on other performance metrics. In some embodiments, the user may select what performance metrics to use on the calculator screen 900.

Thus, as described above, the fields or metrics shown in both the current performance metrics fields 910 and the target performance metrics fields 915 may vary with the sport or the selection of the user. However, the calculator screen 900 will show a selection of performance metrics with both the current performance metrics fields 910 and the target performance metrics fields 915. The selection of performance metrics may be the same in each of the current and target performance metrics fields 910 and 915, respectively, so as to allow the user to be able to directly compare pre-fitness program metrics and post-fitness program metrics, though the performance metrics in the current and target performance metrics fields 910 and 915 do not need to be the same.

The values in the target performance metrics fields 915 may be user editable or calculated by the software application. For example, the user may input a target force metric, and the software application may calculate and determine the target 40 yard dash time, the number of strides in the 40 yard dash, and the vertical jump height. As shown in calculator screen 900*b*, the user may enter a desired target 40 yard dash time as indicated by 911, and the app may calculate the remaining values of the target performance metrics fields 915 based on the desired target time. These calculations may be made based on the desired user input metric in comparison to the corresponding current performance metric. For example, as shown in FIG. 9, the user input desired target 40 yard dash time of 4.61 s in the target performance metrics fields 915 may be compared, by the software application, with the current 40 yard dash time of 5.09 s in the current performance metrics fields 910. The app or the fitness program system 105, knowing the user profile information as entered by the user for the user profile screen 400, may determine the target force metric that would be used to attain the user desired 40 yard dash time, and use that determined target force metric to determine the remaining target performance metrics fields 915, regardless of which target performance metric field the user inputs. This allows the user to choose a target performance metric for any of the available performance metrics.

As discussed above, any of the values in the current performance, metrics fields 910 or the target performance metrics fields 915 may be calculated or computed given either the user's force metric or one of the other performance metrics fields. This shows another exemplary benefit of the invention described herein. The fitness program may be configured to generate the user's force metric based on the user profile information 405 described above in relation to FIG. 4 given any performance, metric. For example, given the user's current 40-yard dash time, the fitness program may generate the user's force metric. The fitness program may then use the generated force metric to determine or calculate predicted values for any of the remaining target performance metrics fields 915. These predicted values may be calculated using the equations. These equations allow the fitness program to be over 99% accurate in predicting the user's physical metrics given the user's force metric and over 99% accurate in predicting the amount of time necessary to improve the user's force metric, as will be discussed in further detail below.

Additionally, the user name field 906 may be generated from the user profile information fields 415 and may identify the user whose calculator screen 900 is displayed. The target time field 920 may include the predicted amount of time the fitness program will use to reach the target performance metrics 915. The target time field 920 may not be editable by the user, but rather may be computed or calculated by the app. In some embodiments, the target time field 920 may be editable by the user, and the values of the target performance metrics fields 920 may be adjusted by the app to show the maximum performance metrics that are attainable in the user specified target time field.

FIG. 10 shows an example of a screenshot of a fitness program overview screen 1000 of the software application that may be active on the electronic device 200 of FIG. 2, in accordance with an exemplary embodiment. The overview screen 1000 may include a label indicating it is the overview screen. The overview screen 1000 may show an overview of the time the fitness program may use to reach the target performance metrics as indicated in the calculator screens 900*a* and 900*b*. The overview screen 1000 includes a menu button 405 as described above in reference to FIG. 4. The overview screen 1000 also includes the target time field 920.

Below the target time field 920, the overview screen 1000 shows a breakdown of the target time into subfields. For the fitness program generated for the user shown in FIG. 10, a target time breakdown 1005 is shown. The target dine breakdown 1005 includes five subfields: a three week strength phase 1010, a one week deload phase 1011, a three week force metric phase 1012, another one week deload phase 1013, and a final three week force metric phase 1014.

Between the three week force metric phase 1012 and the one week deload phase 1013 may be a retest phase where the user may retest their force metric by way of the hex bar dead lift at a maximum weight. The retest phase may represent a self-evaluation where the user re-evaluates their force metric. In some embodiments, the user may re-evaluate the force metric every day of the fitness program, or once every week of the fitness program, or at some other interval. The re-evaluated force metrics may be used by the fitness program system 105 to update or modify the user's fitness program, which may include generating new exercise regimens or a new target time for completion of the fitness program.

In some embodiments, the user may be unable to edit any of the values on the overview screen 1000. In some embodiments, the user may be able to edit any of the values on the overview screen 1000, which may result in the app modifying the remaining values. In some embodiments, the software application may provide a warning or indicator to the user if the user tries to change a value on the overview screen 1000 that is not realistic or possible. In some embodiments, the number of weeks or the phases shown in the target time breakdown 1005 may vary based on the type of sport or position selected by the user in relation to the user profile information fields 415 of the user profile screen 400 of FIG. 4. In some embodiments, more or fewer subfields of the target time breakdown 1005 than shown in FIG. 10 may exist on the fitness program overview screen 1000.

The target time of the target time field 920 may be broken down into more or fewer subfields than those shown on the overview screen 1000. In some embodiments, the target time of the overview screen 1000 may be broken down by number of days or any other increment of time. In some embodiments, where delays have been introduced or where other factors may have changed the predicted target time field 920, the change from the initial predicted target time to the current predicted target time may be displayed for the user.

FIG. 11 shows an example of a screenshot of a training schedule screen 1100 of the app that may be active on the device of FIG. 2, in accordance with an exemplary embodiment. The training schedule screen 1100 may include a label indicating to the user that the training schedule screen is being viewed. The training schedule screen 1100 also includes a menu button 405 as described in reference to FIG. 4 above. The training schedule screen 1100 also includes a view of a calendar 1105. In some embodiments, the calendar 1105 displayed may be a weeklong calendar (as shown in FIG. 11), a month long calendar, a single day calendar, or a calendar of any other period of time. The training schedule screen 1100 may also allow the user to select a day (or another subset of time) 1106 from the displayed calendar 1105 for which a summary of the schedule exercise regimen for the selected subset of time 1106 is displayed below. Below the displayed calendar 1105, a description 1110 of the calendar 1105 displayed on the training schedule screen is shown, below which is shown an exercise regimen overview 1115 and the revised target time field 1120. Next to the exercise regimen overview 1115 are completion boxes 1125, 1126, and 1127.

As shown in FIG. 11, the calendar 1105 may represent a week from October 19 to October 25. Additionally, FIG. 11 shows the subset of time 1106 selected as Wednesday, October 22. Additionally, the description 1110 may indicate that the day 1106 is Wednesday, October 22, which is part of the "Force Number Phase 1—Week 1," which may correspond to the first week of the three week force metric phase 1012 of FIG. 10. In FIG. 11, the exercise regimen overview 1115 shown below the description 1110 may correspond to one or more of the subfields displayed in FIG. 10. For example, the exercise regimen overview 1115 shown includes an overview including a "Dynamic Warm Up" set of exercises, a "Speed" set of exercises, and a "Weightlifting" set of exercises.

The completion boxes 1125, 1126, and 1127 are used to acknowledge the completion of the exercises of the exercise regimen overview 1115. For example, if the "Dynamic Warmup" completion box 1125 is checked (as shown in the FIG. 11), then the app and/or the fitness program knows the user has completed all of the exercises associated with that exercise set. Similarly, the check in the "Speed" completion box 1126 is checked, the app or the fitness program knows the user has completed all of the exercises associated with that exercise set. However, when the "Weightlifting" completion box 1127 is not checked, the app or the fitness program may assume that the user has not completed all of the exercises associated with that exercise set and may automatically generate a revised target time to completion to place in the revised target time field 1120. Thus, as shown in FIG. 11, the revised target time field 1120 shows 12 weeks until the target metrics will be reached, as compared to the 11 weeks indicated in the target time field 920 as shown in FIGS. 9 and 10.

Alternatively, the completion boxes 1125, 1126, and 1127 (or similar boxes) may indicate the user's ability to proceed with the indicated exercises. As discussed above, the fitness program may be configured to lock or unlock exercises or activities based on a determination that the user's body (for example, the central nervous system) is not in a condition to fully benefit from the scheduled exercises. Thus, the completion boxes 1125, 1126, and 1127 (or similar boxes) may indicate whether or not a set of exercises is locked or unlocked. A check nark may indicate that the exercises or activities are accessible, while a "X" may indicate that exercises or activities are locked. When one or more exercises or activities are locked and cannot be performed, the target time field 1120 may be updated to reflect the change. As described above, the fitness program may lock or unlock exercises or other activities based on the user's performance of an exercise on the given day. Thus, as shown in FIG. 11 by the "X" in the completion box 1127, the fitness program may have locked the "Weightlifting" exercises based on the user's performance of the hex bar deadlift in the warm up of the weightlifting exercise. As described above, if the user is unable to lift within 90-100% of his maximum hex bar deadlift weight, then the fitness program may determine that the user's body (for example, central nervous system) is not ready for the next force metric improving workout. This may be caused by the user's body not being sufficiently rested or having not recovered from the previous workout or based on other stresses that may be placed on the user's body outside of the fitness program (for example, stresses from children or work or accidents, etc.). Thus, the fitness program may be personalized down to the daily requirements and capabilities of the user, accounting for any stressful life experiences, etc., that the user may face.

Figure 12:
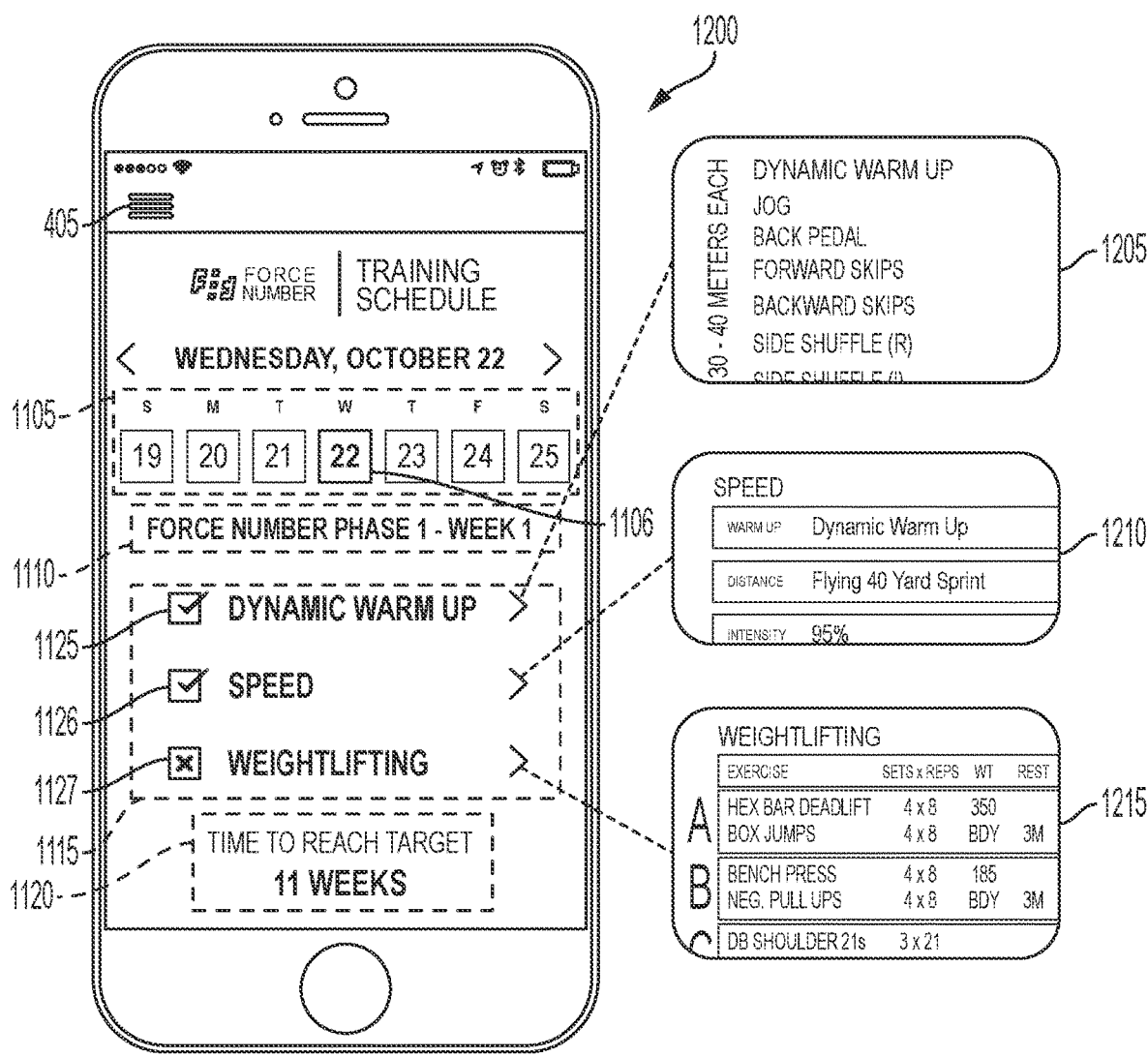
FIG. 12 shows an example of a screenshot of the training schedule overview screen of FIG. 11 with further screenshots of the screens associated with each of the indicated scheduled activities, in accordance with an exemplary embodiment.

FIG. 12 shows an example of a screenshot of the training schedule screen 1100 of FIG. 11 with further screenshots of the screens associated with each of the indicated scheduled activities, in accordance with an exemplary embodiment. The training schedule screen 1100 shown in FIG. 12 includes all of the components described above in relation to FIG. 11. Additionally, FIG. 12 provides the user the ability to select the exercises summarized in the exercise regimen overview 1115 to view more detailed information regarding those summaries. For example, as shown in FIG. 12, when the user selects the "Dynamic Warmup" label, a window may be displayed showing the user the exercises contained in that set of exercises. As shown in window 1205, the set of exercises may include one or more exercises to be performed by the user according to instructions provided within the window.

In some embodiments, the selection of one of the sets of exercises from the exercise regimen overview 1115 may navigate the software application to another screen (not shown in this figure). Each of the sets of exercises from the exercise regimen overview 1115 may have a dedicated window or screen, or may be accessible on a single window or screen using other navigation buttons. Similarly to window 1205, windows 1210 and 1215 may display the exercises contained in the "Speed" set of exercises and the "Weightlifting" exercises, respectively when the "Speed" and "Weightlifting" labels are selected by the user. In each of these windows 1205, 1210, and 1215, the user may have the ability to select the individual exercises for instructions or details on how to complete the exercise (not shown in this figure). Additionally, the windows may include information regarding the number of repetitions for each exercise or the amount of time to spend doing each exercise. In some embodiments, the fitness program system 105 may determine the number of repetitions for each exercise based on the user's initial performance metric, the target performance metrics, and stored information in the exercise data store 110. The stored information may include details about how much each repetition may impact the user's performance metrics and may be used by the fitness program system 105 to determine how many repetitions of various exercises may be used to reach the user's target performance metrics. The fitness program may also determine the number of repetitions for each exercise for the user to perform. Additionally, the user may have the ability to mark each of the individual exercises of the windows 1205, 1210, and 1215 as completed, which may be transferred to the checkboxes 1125, 1126, and 1127 on the exercise regimen overview 1115, such that the app or the fitness program may automatically update the target time field 920 or 1120 based on the user's completion of individual exercises of the screens 1205, 1210 and 1215.

Though not shown in this figure, each of the Dynamic Warm Up, Speed, and/or Weightlifting sets of exercises may begin with one or more exercises intended to help determine if the user is in a condition to fully benefit from the set of exercises. For example, if the user's aerobic system has not recovered from a previous workout or if the user has a chest cold, then the speed exercises may be determined to not be useful as the user will not benefit from them at that given moment. Similarly, as discussed above, a user's central nervous system may not be able to benefit from the weightlifting exercises. Thus, FIG. 12 may provide a display of details of the exercises being locked or unlocked.

Figure 13B:
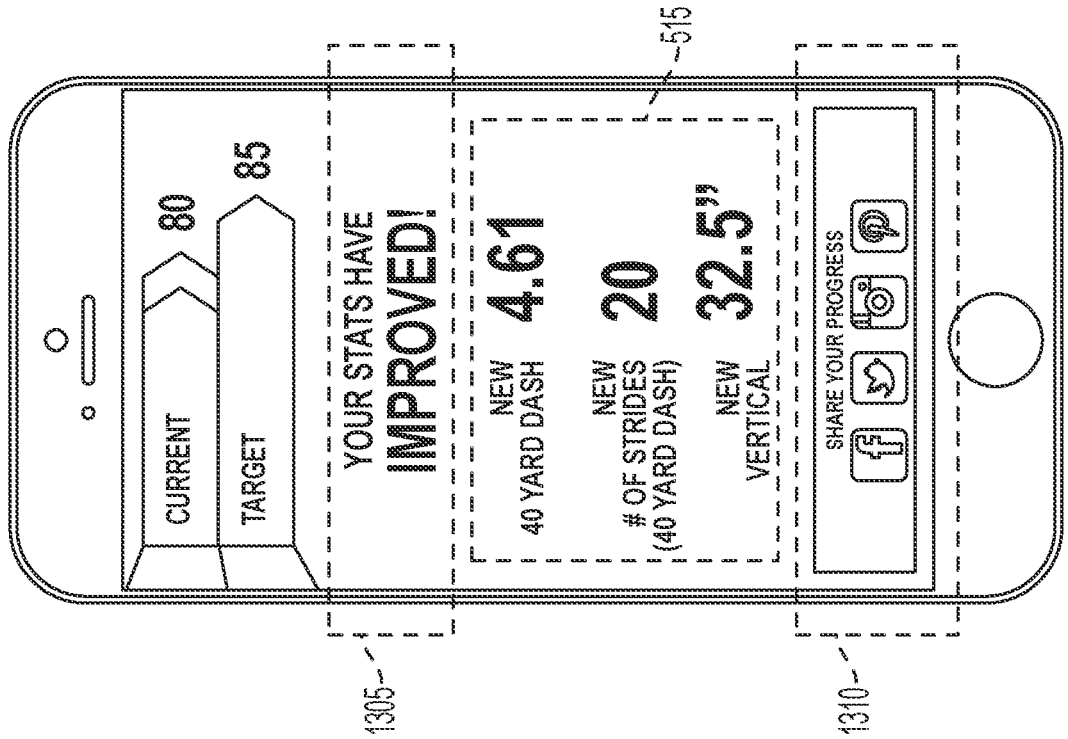
FIGS. 13A and 13B show an example of a screenshot of a progress screen of the software application that may be active on the device of FIG. 2, in accordance with an exemplary embodiment.
Figure 13A:
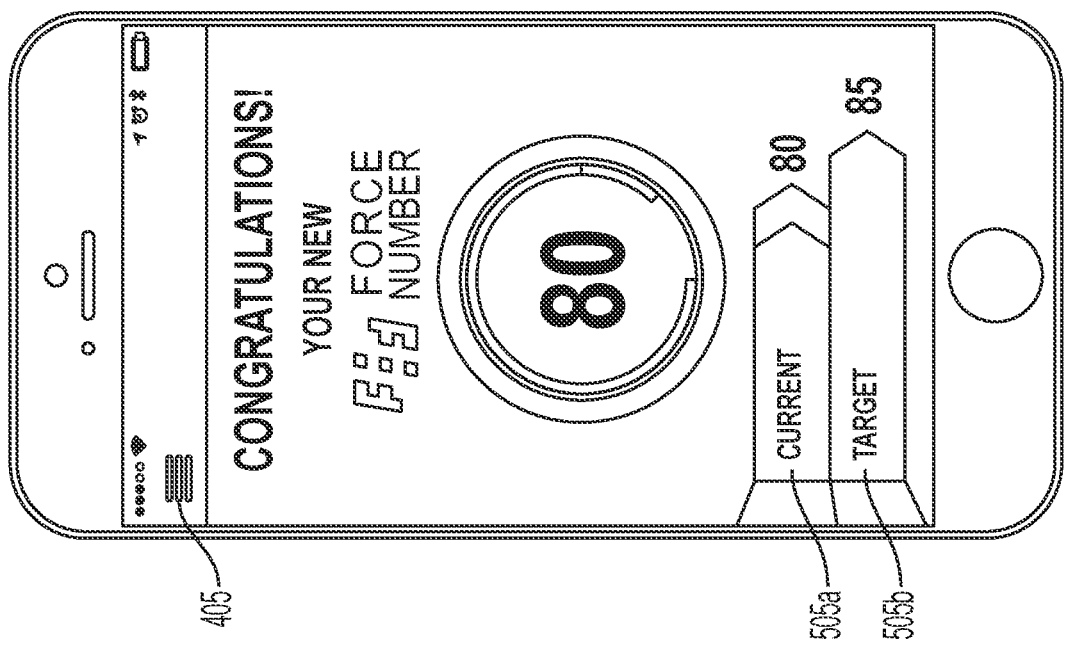

FIGS. 13A and 13B show an example of a screenshot of a progress screen 1300 of the software application that may be active on the device of FIG. 2, in accordance with an exemplary embodiment. The progress screen 1300 may include many of the same elements as the initialization screen 500 described above in reference to FIGS. 5A and 5B; additionally, as noted with reference to FIGS. 5A and 5B above, the progress screen 1300 may be scrollable. In addition to the menu button 405, the current force metric 505a represented by the two indicators, the bar graph-type indicator and the pie chart-type indicator, and the target force metric 505b, represented by the bar-graph-type indicator, and the current performance metrics field 515, the progress screen 1300 may also include a message 1305 to the user and options 1310 to share the user's results.

The elements displayed on the progress screen 1300 that are identical to the elements displayed on the initialization screen 500 will not be described again here. The message 1305 to the user may be customized by the software application according to the user's progress in the fitness program. For example, as shown in FIG. 13, the user has increased the current force metric from "74" as shown in FIG. 5A to "80" as shown in FIG. 13A. Accordingly, as the user has increased the force metric, the message 1305 may indicate the increase or improvement of the user's force metric by displaying "Your Stats Have Improved!" Alternatively, if the user's force metric has declined or stayed the same, the message 1305 may indicate a decline or a plateau. Additionally, the options 1310 may provide the user the ability to share the results shown on the progress screen 1300. For example, the options 1310 may include buttons to share the user's progress via social media websites or applications (for example, Facebook™, Twitter™, Instagram™, or Pinterest™, etc.) or to e-mail or text message the results to a recipient of the user's choosing. In some embodiments, the options 1310 may include any available method of sharing information with other users, and may utilize the third party integration I/O 204 as referenced in FIG. 2. The values in the current performance metrics field 515 may match the values from the target performance metrics field 915 of FIG. 9 with up to 99.7% accuracy, thanks to the calculations and equations described above.

Figure 14:
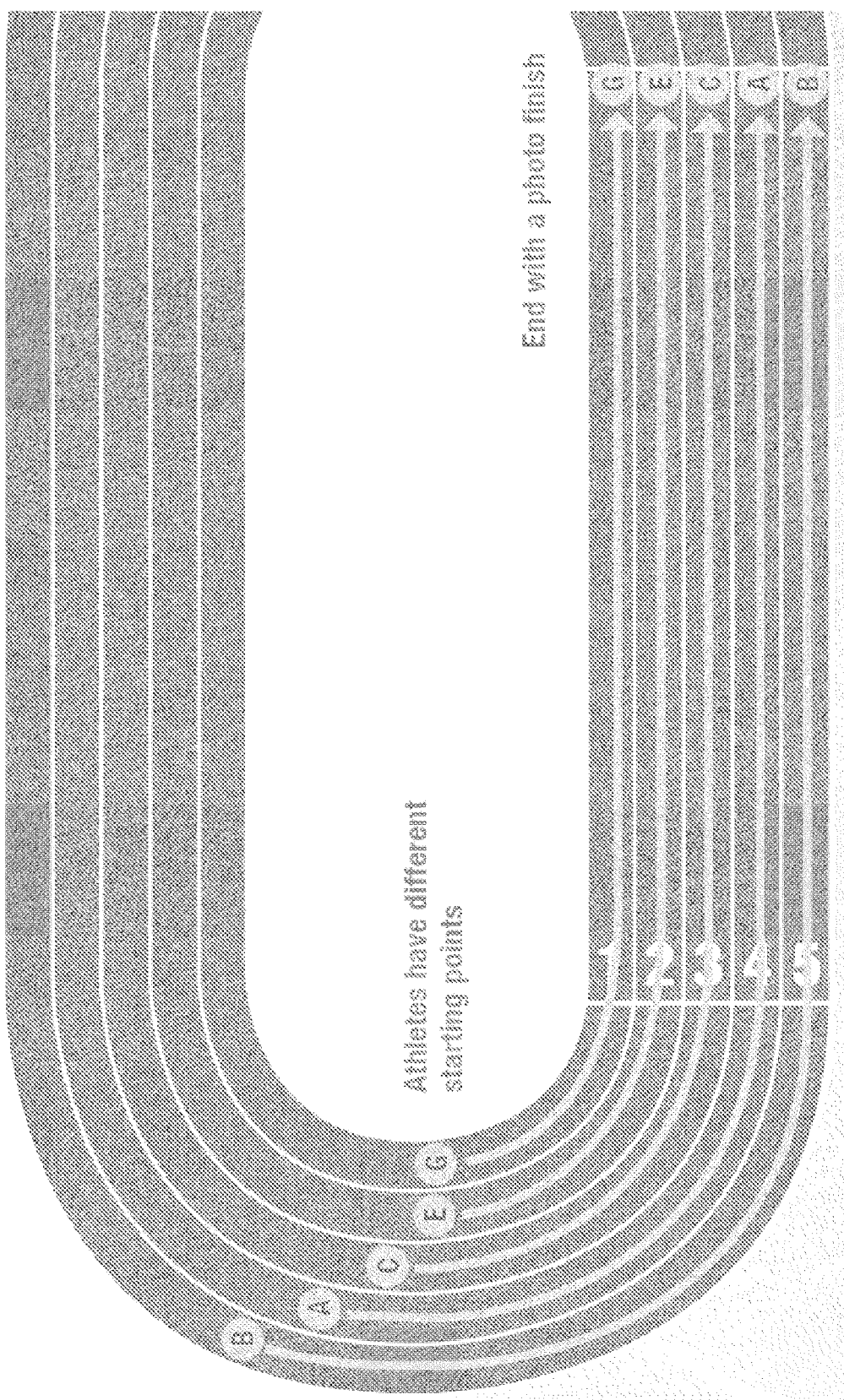
FIG. 14 shows an example of a predictive application of the personalized fitness system described in relation to FIG. 1, in accordance with an exemplary embodiment.

FIG. 14 shows an example of a predictive application of the personalized fitness system described in relation to FIG. 1, in accordance with an exemplary embodiment. As described above, the fitness program system 105 described herein generates a personalized fitness program for a user based on the user's initial user information and initial performance metrics. These generated fitness programs may be up to 99.7% accurate in predicting the user's performance metrics given the initial user information and the user's force metric. The initial performance metrics may include a user's weight, a user's times for specific distance runs, a user's maximum hex bar dead lift weight, or a user's maximum developed force as measured by shoe or other clothing sensors, among other information. Using these initial values and information, the fitness program system may generate the personalized fitness program to allow the user to attain a user selected target result. For example, if the user's initial 40 yard dash time is 5.9 seconds, and the user desires to attain a 40 yard dash time of 4.5 seconds, the fitness program system will generate the personalized fitness program to allow the user to reach the desired goal. The fitness program system 105 will determine the proper exercises to include in the generated exercise regimen to ensure the user attains the goal. In making this determination, the fitness program system 105 may analyze stored data of other users' capabilities at given performance metrics and initial values and information and data acquired by the fitness program system through the software application running on the user's mobile device 120, for example an app on the user's phone, a program on the user's computer, or an operating system of a dedicated fitness program device.

One exemplary benefit of the software application and the fitness program system is the ability to predict outcomes given the users' force. For example, as shown in FIG. 14, given the force metrics of five athletes, the fitness program system 105 can predict the physical capabilities of the athletes with such accuracy that it may be able to place the five athletes at different, calculated distances on the track such that the five athletes will all cross the finish line at the same time. The fitness program system 105 is 99.7% accurate in these calculations and determinations, and may place the five athletes at specific locations with a specificity of 1 cm. As shown in FIG. 14, athlete G may have the lowest force metric, with athlete E having a slightly larger force metric than athlete G but a slightly smaller force metric than athlete C. Athlete C may have a smaller force metric than athlete A, who has a smaller force metric than athlete B. From viewing FIG. 14, we see that athlete G has the shortest distance to run being in the most inside lane of the track depicted. Using the equations described above, the fitness program may be able to determine, given the athlete G's force metric and either the distance to run to the finish line, the amount of time it will take athlete G to reach the finish line. Then this time may be used, in conjunction with the force number of athlete E, to determine at what distance from the finish line the athlete E should be placed to reach the finish line at the same time as athlete G. Similarly, the starting positions for the athletes C, A, and B may each be determined.

Figure 15:
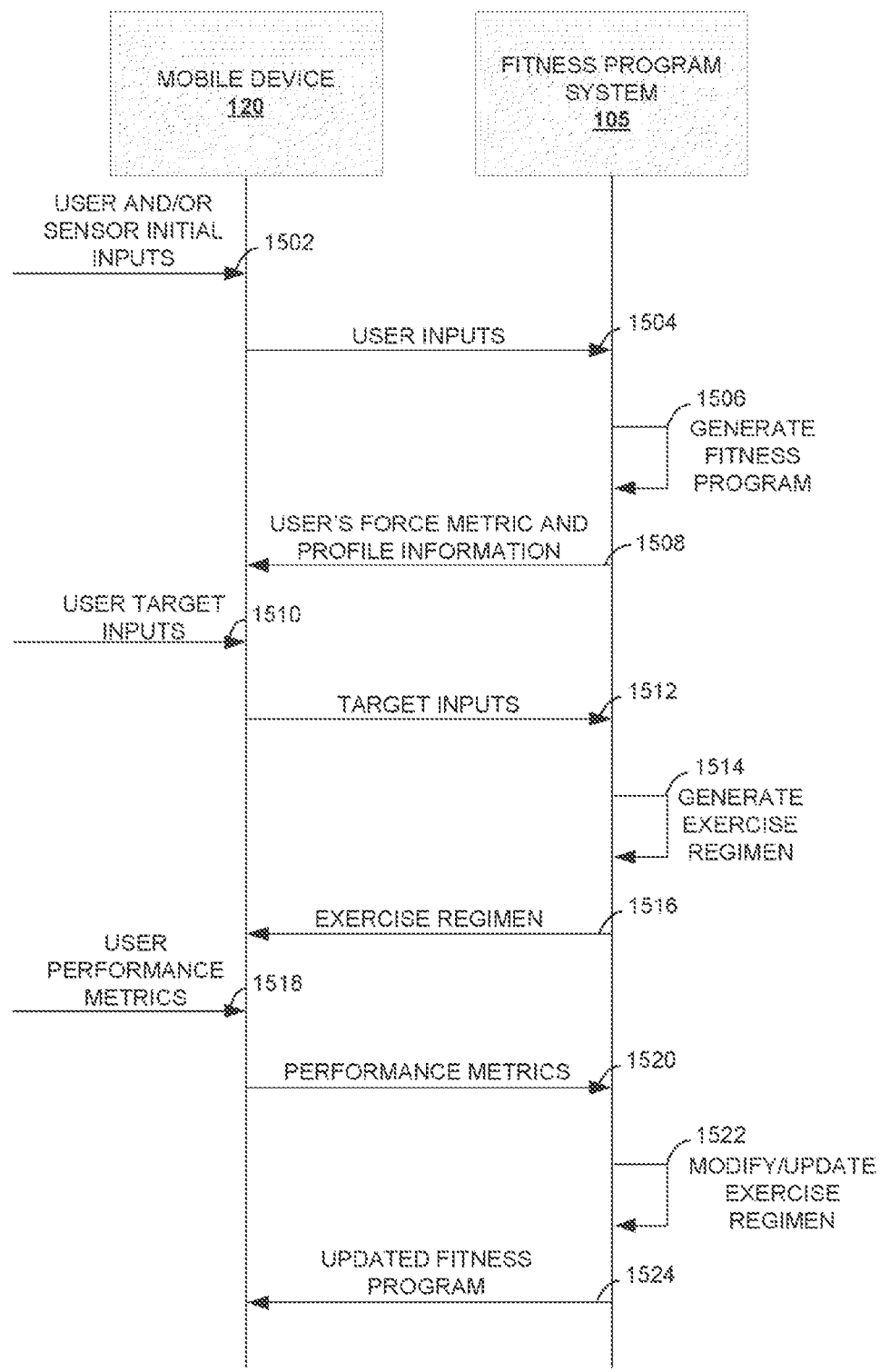
FIG. 15 shows a message diagram of an example of communications that may take place between components of the network diagram of FIG. 1, in accordance with an exemplary embodiment.

FIG. 15 shows a message diagram 1500 of an example of communication messages that may take sent between components of the network diagram 100 of FIG. 1, in accordance with an exemplary embodiment. The message diagram 1500 depicts the mobile device 120 and the fitness program system 105, comprising the fitness program server 106, the fitness/metric data store 108, the exercise data store 110, and the fitness program data store 112 (though not shown in this figure) and the communication messages that may take place between each of the depicted components. Additionally, the message diagram 1500 depicts actions that are performed by the components or messages or inputs that are received by the components from external components.

The message diagram 1500 may begin with the mobile device 120 receiving a message 1502 comprising user inputs from a user. As described above, in some embodiments this may include the mobile device 120 receiving the user's personal information and measured initial performance metrics and force metric. In some embodiments, the user inputs may include inputs from one or more sensors. The mobile device 120 may receive the user inputs and communicate them to the fitness program system 105 via the network 104 (as referenced in FIG. 1) as message 1504. After receiving message 1504 comprising the user inputs, the fitness program system 105 may use the inputs received to generate a fitness program for the user, which may include internal message(s) 1506. In some embodiments, generating the fitness program may initially comprise generating the user's force metric and the user profile for the fitness for the generated fitness program. The process of generating the fitness program may include utilizing information stored in the force/metric data store 108, the exercise data store 110, and/or the fitness program data store 112.

After the user's fitness program is generated, the fitness program system 105 may send to the mobile device 120 the user's force metric and the generated profile information via message 1508 for display or communication to the user. Then the mobile device 120 may receive the user's target metrics via a message 1510, which the mobile device 120 may communicate to the fitness program system 105 via message 1512. The target inputs may include the desired physical metrics the user hopes to achieve. The fitness program system may use the target inputs received from the mobile device 120 combined with the user inputs received in the message 1504 and the information stored in the force/metric data store 108, the exercise data store 110, and the fitness program data store 112 to generate an exercise regimen associated with the user's fitness program via message 1514.

Once the exercise regimen is generated, the fitness program system 105 may send the exercise regimen, via message 1516, to the mobile device 120 for display to the user who is participating in the fitness program. While or after the user performs the exercise regimen, performance metrics associated with the user and the exercise regimen may be input to the mobile device 120 via message 1518. The performance metrics may include the times, weights, etc., that the user attained in their latest self-evaluation or in the latest exercises performed. The mobile device 120 may communicate these metrics to the fitness program system 105 via message 1520. The fitness program system 105 may use the exercise regimen metrics to update the previously generated fitness program, for example updating a target completion date or updating the exercise regimen in light of the completed exercises, for example via internal messages 1522. After updating the fitness program, the fitness program system 105 may communicate the updated fitness program to the mobile device 120 via message 1524, which may display or otherwise communicate the updated fitness program to the user. In some embodiments, more or fewer messages may be used in the message diagram 1500 than shown here or more components may participate directly in the message diagram 1500 though not shown in FIG. 15.

Figure 16:
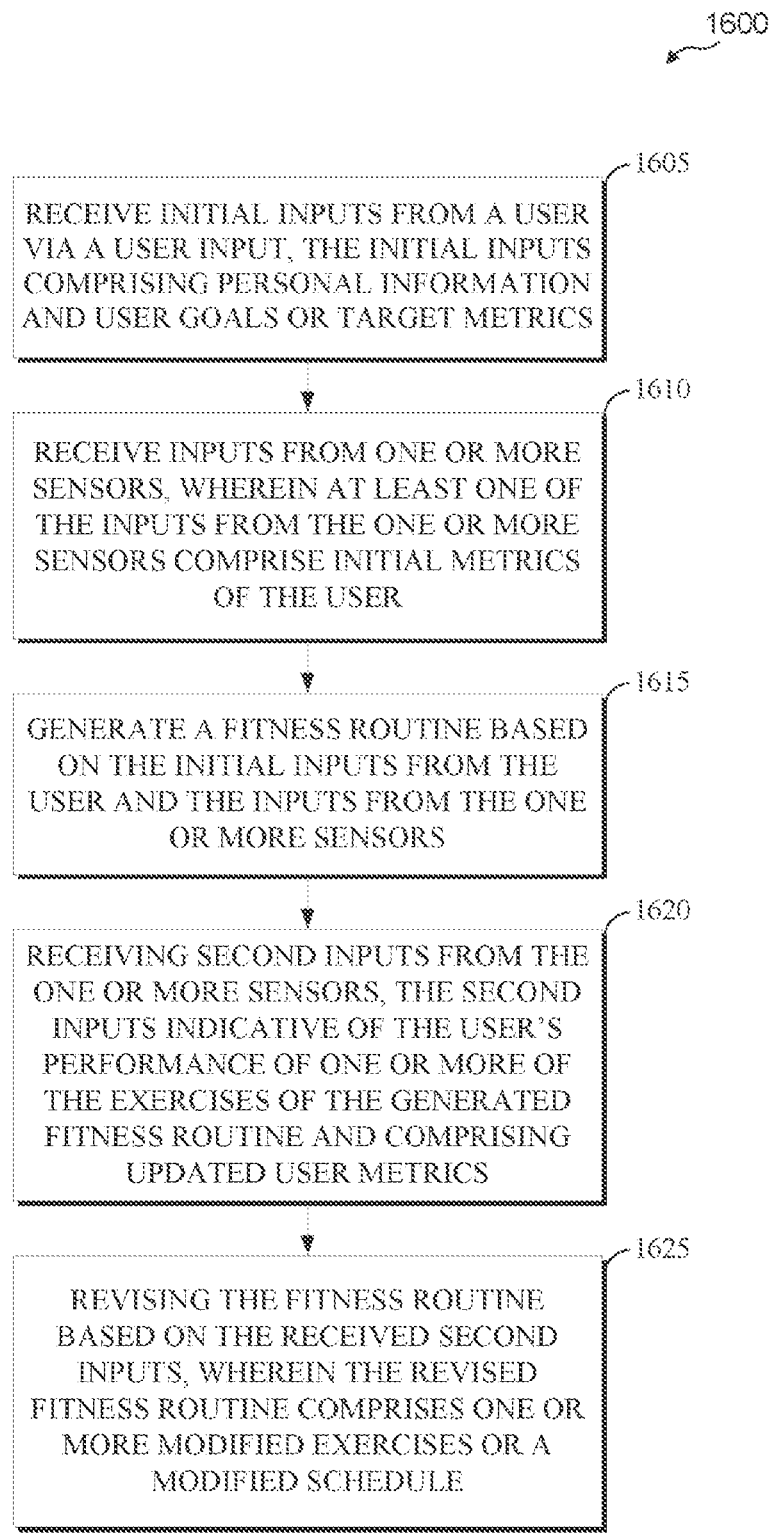
FIG. 16 shows a flow chart of an exemplary method of generating a fitness program as described in relation to FIG. 1, in accordance with an exemplary embodiment.

FIG. 16 shows a flow chart of a method 1600 of generating a fitness program as described in relation to FIG. 1 in accordance with an exemplary embodiment. The method 1600 of FIG. 16 may be implemented by the fitness program system described above, for example the electronic device 200 when configured to operate as the fitness program system. The method 1600 may start at block 1605. Block 1605 may include receiving initial inputs from a user via a user input, for example, a keyboard, a mouse, or a touchscreen or like device. The initial inputs may include personal information and user goals or target metrics. In some embodiments, the initial inputs may include user profile type information, including information regarding the gender, height, weight, and the sport in which the user participates. After receiving the user inputs at block 1605, the method 1600 may progress to block 1610.

At block 1610, the method may include receiving inputs from one or more sensors, wherein at least one of the inputs from the one or more sensors include initial metrics of the user. The inputs from the one or more sensors may include information or metrics from a shoe sensor or some other sensor that may be worn or embedded into the user's clothes or exercise equipment. In some embodiments, these inputs may include initial metrics of the user, for example the user's max hex bar dead lift weight or the user's speed in a 40 yard dash, among others. After receiving the input from the sensors, the method 1600 may proceed to block 1615.

At block 1615, the method 1600 may include generating a fitness routine based on the initial inputs from the user and the inputs from the one or more sensors, wherein the fitness routine includes one or more exercises selected for the generated fitness routine based on at least one of the personal information, goals, initial metrics and target metrics of the user. Generating the fitness routine may also include generating a schedule according to which the user may perform the selected one or more exercises. Additional details regarding the generating of the fitness routine are described in relation to FIG. 17 below. An additional step of block 1615 may comprise determine the predicted target completion time. After generating the fitness routine, the method 1600 may proceed to block 1620.

At block 1620, the method 1600 receives second inputs from the one or more sensors, the second inputs indicative of the user's performance of one or more of the exercises of the generated fitness routine and comprising updated user metrics. In some embodiments, the second inputs may be indicative of the user having engaged in an exercise of the scheduled fitness program or in an unscheduled exercise. The sensors may provide metrics regarding the user's performance of the exercise to the fitness program. Based on the inputs from these sensors, the fitness program system may revise or modify the fitness program at block 1625. Block 1625 includes revising the fitness program based on the received second inputs, wherein the revised fitness program includes one or more modified exercises or a modified schedule. Revising the fitness program may include at least one of modifying at least one of the schedule exercises of the fitness program or the schedule according to which the is to perform the exercises or activities.

Figure 17:
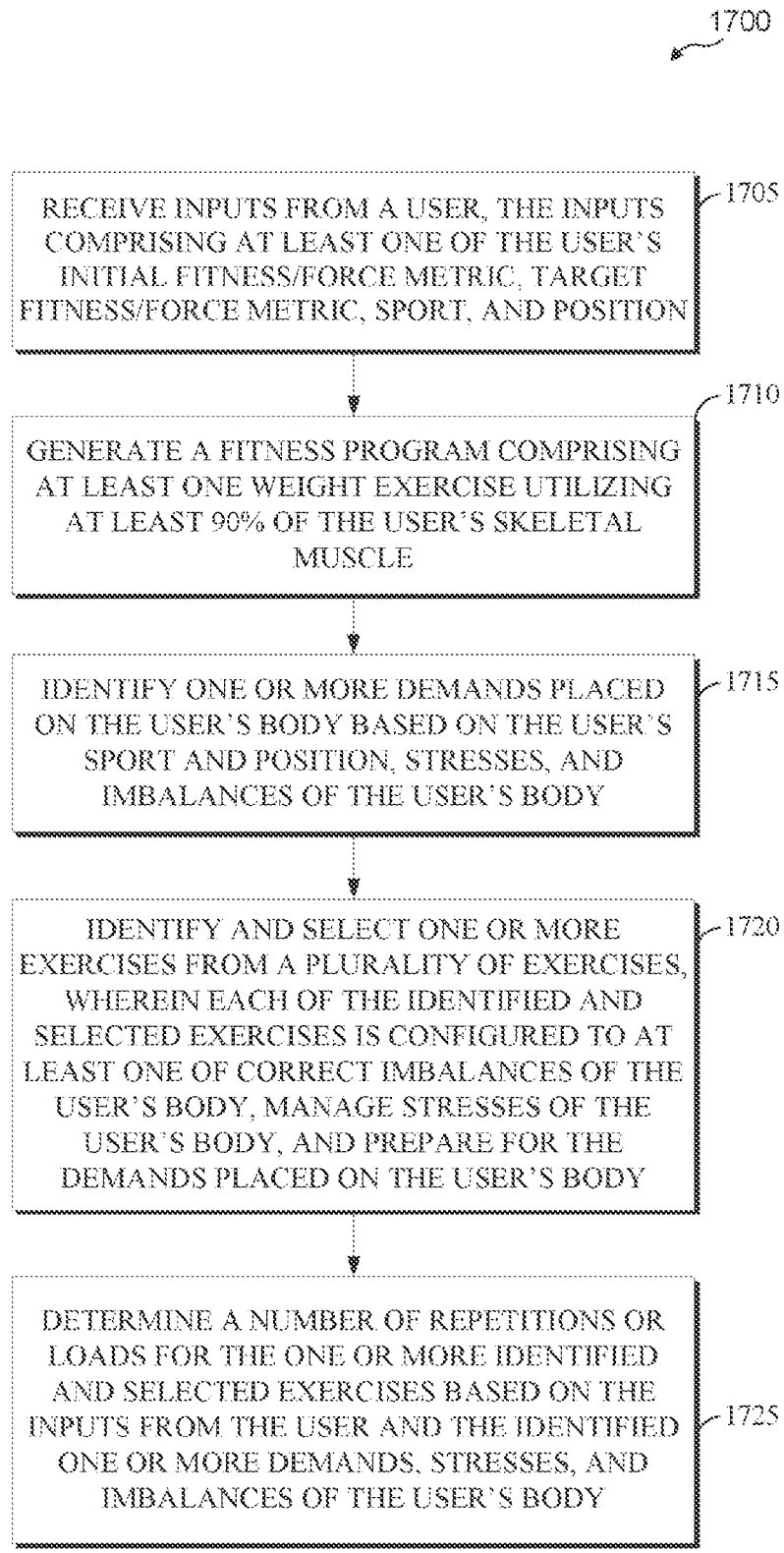
FIG. 17 shows a flow chart providing further details of a method for generating the fitness program described in FIG. 16, in accordance with an exemplary embodiment.

FIG. 17 shows a flow chart providing further details of a method 1700 for generating the fitness program described in method 1600 of FIG. 16, in accordance with an exemplary embodiment. The method 1700 of FIG. 17 may be implemented by the fitness program system described above, for example the electronic device 200 when configured to operate as the fitness program system 105. The method 1700 may start at block 1705. Block 1705 may include receiving the initial inputs from the user via the user input, for example, a keyboard, a mouse, or a touchscreen or like device (as described by block 1605 of FIG. 16 above). The initial inputs may include personal information and user goals or target metrics. The initial inputs may also include the user's sport and/or position played in the sport, which may be used to select specific exercises and activities for the fitness program to be generated. As described above, in some embodiments, the initial inputs may include user profile type information, including information regarding the gender, height, weight, and the sport and/or position in which the user participates. In some embodiments, the initial inputs may comprise information received from the peripheral electronic devices 122, for example the shoe sensors. This received information may be used to determine the user's force metric (as described above). Receiving the inputs may also comprise determining the desired improvement of the user's force metric by comparing the target force metric and the initial force metric. After receiving the user inputs (and determining the force metric improvement) at block 1705, the method 1700 may proceed to block 1710.

At block 1710, the method 1700 may generate a fitness program comprising at least one weight exercise that utilizes at least 90% of the user's skeletal muscle. For example, as described above, this weight exercise may comprise a hex bar deadlift at the user's maximum weight. As described above, the user's maximum hex bar deadlift weight may comprise the weight that the user can lift for only one or two repetitions (reps). Thus, the generated fitness program may include the maximum hex bar deadlift lifting exercise at the user's maximum weight. Such an exercise may serve the purpose of testing the user's force metric for that day and also help to improve the user's strength and ability to lift heavier loads. In some embodiments, other exercise that utilizes at least 90% of the user's skeletal muscle may be used (for example, a machine that targets the user's skeletal muscle or that may help the user utilize at least 90% of the skeletal muscle). After the fitness program is generated with the at least one weight exercise, then method 1700 progresses to block 1715.

At block 1715, the method 1700 may identify one or more demands placed on the user's body based on the user's sport and position, stresses, and imbalances of the user's body. For example, as discussed above, the method 1700 may identify that the user's right and left legs generate different forces. In some embodiment, such an imbalance may lead to or increase risk of injury, for example an ACL or similar injury. Additionally, demands on the user's body may change based on the sport or position of the user. For example, a baseball player that is a catcher may have different demands placed on the body than a pitcher. The different demands and stresses may increase different risks of injury or may provide for different potential benefits for a user. Once the one or more demands or stresses or imbalances of the user's body are identified, the method 1700 proceeds to block 1720.

At block 1720, the method 1700 identifies and selects one or more exercises from a plurality of exercises of the exercise data store 110 of FIG. 1 that may be used to help the user manage the identified demands, stresses, or imbalances from block 1715. In some embodiments, this may comprise the dynamic warm up or speed exercises discussed in relation to FIGS. 11 and 12. In some embodiments, the identified and selected exercises may comprise the stretches as discussed in reference to FIG. 6 or exercises to correct imbalances in the force production of each leg or the front/back of each leg, as referenced in FIG. 8. If more than one demand, stress, or imbalance is identified in the user's body, then the method 1700 may identify and select one or more exercises targeting each of the one or more demands, stresses, or imbalances. Once the exercises are identified and selected, the method 1700 proceeds to block 1725.

At block 1725, the method 1700 determines a number of repetitions or loads for the one or more identified and selected exercises based on the initial inputs from the suer and the identified one or more demands, stresses, and imbalances of the user's body. For example, the method 1700 may determine that the user should perform the hex bar deadlift at a weight of 350 pounds for four sets of 8 reps each, as shown in FIG. 12. In some embodiments, to correct an imbalance in the user's stature, different stretches may be prescribed, or to correct imbalances in forces generated by different muscles, certain muscles may be targeted for one or more additional exercises to equalize the generated forces. Once the number of repetitions for each exercise is determined, the method 1700 generating the fitness program will be complete.

FIG. 18 shows a flow chart providing details of a method 1800 for updating or modifying the fitness program described in methods 1600 of FIG. 16 and 1700 of FIG. 17, in accordance with an exemplary embodiment. The method 1800 of FIG. 18 may be implemented by the fitness program system described above, for example the electronic device 200 when configured to operate as the fitness program system 105. The method 1800 may start at block 1805. At block 1805, the method 1800 may present the user with the initial exercise or activity of the day as determined by the generated fitness program for the user to perform. As described above, for a weightlifting exercise routine, the initial exercise may be a maximum hex bar deadlift to ensure the body is in condition to benefit from the scheduled workout, while for speed or endurance exercise routine, the initial exercise may be a warmup run. After presenting the user with the initial exercise, the method 1800 proceeds to block 1810.

At block 1810, the method 1800 receives inputs from the user or peripheral sensor electronics to update the generated fitness program. The inputs received at block 1810 may comprise performance metrics of the user for the initial exercise or activity. These inputs may allow the method 1800 to determine if the user's body is capable of fully benefitting from the scheduled exercises and activities based on the user's performance of the initial exercise or activity at block 1815. As discussed above, this determination at block 1815 may comprise comparing the user's results from the initial exercise or activity with previous results from the same or similar exercises (for example the maximum weight for the hex bar deadlift compared with the user's initial or more recent hex bar deadlift maximum weight). If the user's performance as indicated by the received inputs is within 90-100% of the user's maximum initial or previous performance, then the method 1800 may proceed to block 1820. If the user's performance is not within 90-100% of the user's maximum initial or previous performance, then the method 1800 may proceed to block 1830. In some embodiments, the 90-100% ranges may be replaced with any other ranges, for example 85-100% or 85-95% or 80-95%, etc.

At block 1820, the method 1800 may unlock the remaining exercises and activities for the user to perform and scheduled. Then, the method 1800 proceeds to block 1825 and updates the fitness program based on the user's performance of the scheduled exercises and updates the predicted target date based on one or more of the user's initial fitness/force metrics, current fitness/force metrics, target fitness/force metrics, and the user's place in the fitness program. This method 1800 may be repeated for each day of the fitness program and each different exercise routine of the fitness program.

At block 1830, method 1800 locks the remaining activities and exercise from the user. This is because the exercises and activities scheduled would be wasted because the user would not fully benefit from the exercises. Accordingly, the method 1800 would proceed to block 1835 and update the fitness program based on the user's inability to perform the scheduled exercises. For example, when the user is locked from performing an exercise or activity, the fitness program may update the subsequent day's scheduled activities to include some or all of the locked activities from the present day, thus ensuring the user does not miss the exercises or activities all together. In some embodiments, the fitness program may replace exercises from subsequent days with new exercises that may be more beneficial and that will not require the target date to be extended. In some embodiments, the updating of the fitness program may comprise updating the target date and extending the target date to account for the day where the user was locked from activities. In some embodiments, if the fitness program identifies a common routine of locked exercises, the fitness program may automatically adapt the scheduled activities to minimize the number of days that the user is locked from accessing. This automatic reconfiguration of the scheduled activities may result in the predicted target date being changed accordingly.

In some embodiments, the method 1800 may update the fitness program based on the user completing an unscheduled activity that may meet the requirements of one or more of the exercises of the scheduled exercises and activities for a given day. For example, the user may take a pet for a long walk or run that may meet the requirements for one or more of the exercises of the speed or warm-up routines. Accordingly, the method 1800 may be configured to track the user's activities and apply them, as possible, to the scheduled activities and exercises and update the schedule accordingly.

The word "exemplary" is used herein to mean "serving as an example, instance, or illustration." Any embodiment described herein as "exemplary" is not necessarily to be construed as preferred or advantageous over other embodiments. Various aspects of the novel systems, apparatuses, and methods are described more fully hereinafter with reference to the accompanying drawings. This disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein, one skilled in the art may appreciate that the scope of the disclosure is intended to cover any aspect of the novel systems, apparatuses, and methods disclosed herein, whether implemented independently of, or combined with, any other aspect described. For example, an apparatus may be implemented or a method may be practiced using any number of the aspects set forth herein. In addition, the scope of the described features is intended to cover such an apparatus or method which is practiced using other structure, functionality, or structure and functionality in addition to or other than the various aspects of the invention set forth herein. It may be understood that any aspect disclosed herein may be embodied by one or more elements of a claim.

As used herein, the terms "display" or "displaying" encompass a variety of actions. For example, "displaying" may include presenting in audio form, visual form, or some other form that can be made known to the senses. The term may also include a combination of two or more of the foregoing.

Although particular aspects are described herein, many variations and permutations of these aspects fall within the scope of the disclosure. Although some benefits and advantages of the preferred aspects are mentioned, the scope of the disclosure is not limited to particular benefits, uses, or objectives. Rather, aspects of the disclosure are broadly applicable to different personalization technologies, system configurations, networks, and transmission protocols, some of which are illustrated by way of example in the figures and the included description of the preferred aspects. The detailed description and drawings are merely illustrative of the disclosure rather than limiting, the scope of the disclosure being defined by the appended claims and equivalents thereof.

The terms "processor" and "processor module," as used herein are a broad terms, and are to be given their ordinary and customary meaning to a person of ordinary skill in the art (and are not to be limited to a special or customized meaning), and refer without limitation to a computer system, state machine, processor, or the, like designed to perform arithmetic or logic operations using logic circuitry that responds to and processes the basic instructions that drive a computer. In some embodiments, the terms can include ROM and/or RAM associated therewith.

As used herein, the term "determining" encompasses a wide variety of actions. For example, "determining" may include calculating, computing, processing, deriving, investigating, looking up (for example, looking up in a table, a database or another data structure), ascertaining and the like. Also, "determining" may include receiving (for example, receiving information), accessing (for example, accessing data in a memory) and the like. Also, "determining" may include resolving, selecting, choosing, establishing, and the like.

As used herein, the terms "provide" or "providing" or "transmit" or "transmitting" encompass a wide variety of actions. For example, "providing" may include storing a value in a location for subsequent retrieval, transmitting a value directly to the recipient, transmitting or storing a reference to a value, and the like. "Providing" may also include encoding decoding, encrypting, decrypting, validating, verifying, and the like.

As used herein, the term "message" encompasses a wide variety of formats for representing information for transmission. A message may include a machine readable aggregation of information such as an XML document, fixed field message, comma separated message, or the like. While recited in the singular, it will be understood that a message may be composed/transmitted/stored/received/etc. in multiple parts.

Any reference to an element herein using a designation such as "first," "second," and so forth does not generally limit the quantity or order of those elements. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may include one or more elements.

Conditional language used herein, such as, among others, "can," "could," "might," "may," "e.g.," "for example," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

The term "or" as used herein is intended to mean an inclusive "or" rather than an exclusive "or." Unless specified otherwise, or clear from the context, the phrase "X employs A or B" is intended to mean any of the natural inclusive permutations. That is, the phrase "X employs A or B" is satisfied by any of the following instances; X employs A; X employs B; or X employs both A and B. In addition, the articles "a" and "an" as used in this application and the appended claims should generally be construed to mean "one or more" unless specified otherwise or clear from the context to be directed to a singular form.

Depending on the embodiment, certain acts, events, or functions of any of the methods described herein can be performed in a different sequence, can be added, merged, or left out altogether (for example, not all described acts or events are necessary for the practice of the method). Moreover, in certain embodiments, acts or events can be performed concurrently, for example, through multi-threaded processing, interrupt processing, or multiple processors or processor cores, rather than sequentially.

The various illustrative logical blocks, modules, circuits, and algorithm steps described in connection with the embodiments disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality can be implemented in varying ways for each particular application, but such embodiment decisions should not be interpreted as causing a departure from the scope of the disclosure.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

The blocks of the methods and algorithms described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, a hard disk, a removable disk, a CD-ROM, or any other form of computer-readable storage medium known in the art. An exemplary storage medium is coupled to a processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

Further, it should be appreciated that modules and/or other appropriate, means for performing the methods and techniques described herein can be downloaded and/or otherwise obtained by a device as applicable. For example, such a device can be coupled to a server to facilitate the transfer of means for performing the methods described herein. Alternatively various methods described herein can be provided via storage means (e.g., RAM, ROM, a physical storage medium such as a compact disc (CD) or floppy disk, etc.), such that a device can obtain the various methods upon coupling or providing the storage means to the device. Moreover, any other suitable technique for providing the methods and techniques described herein to a device can be utilized.

The interfaces shown represent example implementations of a tangible device configured to perform one or more of the features described. The interface elements may be implemented via the execution of machine readable instructions to generate a graphical representation of the interface on a device. The graphical representation may be, for example, a machine readable mark-up language (e.g., HTML), executable machine readable instructions (e.g., Javascript), or combinations of these or other display technologies. In some implementations, the interface may be constructed of physical components such as buttons, circuits, lights, and the like. The interface components may be controlled by a circuit configured to implement the methods described above. In some implementations, it may be desirable to control the interface components via a processor configured to execute stored instructions which cause the interface components to perform aspects of the methods described.

It is to be understood that the claims are not limited to the precise configuration and components illustrated above. Various modifications, changes and variations may be made in the arrangement, operation and details of the methods and apparatus described above without departing from the scope of the claims.

While the foregoing is directed to aspects of the present disclosure, other and further aspects of the disclosure may be devised without departing from the basic scope thereof, and the scope thereof is determined by the claims that follow.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the disclosures described herein can be embodied within a form that does not provide all of the features and benefits set forth herein, as some features can be used or practiced separately from others. The scope of certain disclosures disclosed herein is indicated by the appended claims rather than by the foregoing description. All changes which come within the meaning and range of equivalency of the claims are to be embraced within their scope.

What is claimed is:

1. A footwear system, comprising:
an article of footwear, comprising a wireless transmitter and an electronic sensor, the wireless transmitter configured to wirelessly transmit a sensor signal based on an output form the electronic sensor; and
a wireless receiver, configured to receive the sensor signal from the wireless transmitter;
a processing unit, configure to:
receive the sensor signal from the wireless receiver;
compare the sensor signal as received to a target metric value of a predetermined fitness activity to obtain a comparison;
based on the comparison, cause a user interface to display a real-time adjustment to the predetermined fitness activity.

2. The footwear system of claim 1, wherein the at least one identified target metric value comprises a target force metric value, a target 40 yard dash time, a target vertical jump height, or a target hex bar deadlift weight.

3. The footwear system of claim 2, wherein the electronic sensor is a force sensor and the target metric value is the target force metric value.

4. The footwear system of claim 1, wherein the predetermined fitness activity is a current predetermined fitness activity, and wherein the processing unit is further configured to:
receive the sensor signal from the wireless receiver over a plurality of predetermined fitness activities, including the current predetermined fitness activity;
obtain the comparison based on the sensor signals over the plurality of predetermined fitness activities; and
cause the user interface to display the real-time adjustment to the current predetermined fitness activity.

5. The footwear system of claim 1, wherein the processing unit is further configured to cause the user interface to display a prompt for the user to manually enter a physiological issue and wherein the processing unit is further configured to display the real-time adjustment further based on the physiological issue.

6. The footwear system of claim 1, wherein the processing unit is further configured to:
generate a projected performance based on the real-time adjustment to the predetermined fitness activity being implemented by the user; and
cause the user interface to display the projected performance along with the real-time adjustment.

7. The footwear system of claim 6, wherein the processing unit is further configured to cause the user interface to display an unadjusted projected performance along with the projected performance.

8. A non-transitory computer readable medium, comprising instructions which, when implemented by a processing unit, cause the processing unit to perform operations comprising:
receive a sensor signal based on an output form an electronic sensor of an article of footwear;
compare the sensor signal as received to a target metric value of a predetermined fitness activity to obtain a comparison;
based on the comparison, cause a user interface to display a real-time adjustment to the predetermined fitness activity.

9. The computer readable medium of claim 8, wherein the at least one identified target metric value comprises a target force metric value, a target 40 yard dash time, a target vertical jump height, or a target hex bar deadlift weight.

10. The computer readable medium of claim 9, wherein the electronic sensor is a force sensor and the target metric value is the target force metric value.

11. The computer readable medium of claim 8, wherein the predetermined fitness activity is a current predetermined fitness activity, and wherein the processing unit is further configured to:
receive the sensor signal from the wireless receiver over a plurality of predetermined fitness activities, including the current predetermined fitness activity;
obtain the comparison based on the sensor signals over the plurality of predetermined fitness activities; and
display the real-time adjustment to the current predetermined fitness activity.

12. The computer readable medium of claim 8, wherein the processing unit is further configured to cause the user interface to display a prompt for the user to manually enter a physiological issue and wherein the processing unit is further configured to display the real-time adjustment further based on the physiological issue.

13. The computer readable medium of claim 8, wherein the processing unit is further configured to:
  generate a projected performance based on the real-time adjustment to the predetermined fitness activity being implemented by the user; and
  cause the user interface to display the projected performance along with the real-time adjustment.

14. The computer readable medium of claim 13, wherein the processing unit is further configured to cause the user interface to display an unadjusted projected performance along with the projected performance.

15. A processing unit-implemented method, comprising:
  receiving a sensor signal based on an output form an electronic sensor of an article of footwear;
  comparing the sensor signal as received to a target metric value of a predetermined fitness activity to obtain a comparison;
  based on the comparison, causing a user interface to display a real-time adjustment to the predetermined fitness activity.

16. The method of claim 15, wherein the at least one identified target metric value comprises a target force metric value, a target 40 yard dash time, a target vertical jump height, or a target hex bar deadlift weight.

17. The method of claim 15, wherein the predetermined fitness activity is a current predetermined fitness activity, and further comprising:
  receiving the sensor signal over a plurality of predetermined fitness activities, including the current predetermined fitness activity;
  obtaining the comparison based on the sensor signals over the plurality of predetermined fitness activities; and
  causing the user interface to display the real-time adjustment to the current predetermined fitness activity.

18. The method of claim 15, further comprising causing the user interface to display a prompt for the user to manually enter a physiological issue and wherein the processing unit is further configured to cause the user interface to display the real-time adjustment further based on the physiological issue.

19. The method of claim 15, further comprising:
  generating a projected performance based on the real-time adjustment to the predetermined fitness activity being implemented by the user; and
  causing the user interface to display the projected performance along with the real-time adjustment.

20. The method of claim 19, further comprising causing the user interface to display an unadjusted projected performance along with the projected performance.

* * * * *